United States Patent [19]

Naito et al.

[11] 4,112,228
[45] Sep. 5, 1978

[54] 7-(D-α-HYDROXY-2-ARYLACETAMIDO)-3-(2-CARBOXYALKYL-2,3-DIHYDRO-S-TRIAZOLO-[4,3-b]PYRIDAZIN-3-ON-6-YLTHIOMETHYL)-3-CEPHEM-4-CARBOXYLIC ACIDS AND DERIVATIVES

[75] Inventors: Takayuki Naito, Kawasaki; Jun Okumura, Yokohama; Hajime Kamachi, Ichikawa, all of Japan

[73] Assignee: Bristol-Myers Company, New York, N.Y.

[21] Appl. No.: 777,986

[22] Filed: Mar. 16, 1977

Related U.S. Application Data

[63] Continuation-in-part of Ser. No. 705,226, Jul. 13, 1976, abandoned.

[51] Int. Cl.² ............... C07D 501/54; C07D 501/56; C07D 519/00
[52] U.S. Cl. .................................. 544/26; 544/236; 424/245; 424/246; 544/4; 544/23; 544/27; 560/226; 560/254
[58] Field of Search ............... 260/243 C; 705/226; 544/4 US, 26 US, 27 US, 4, 26, 27

[56] References Cited

U.S. PATENT DOCUMENTS

| 3,641,021 | 2/1972 | Ryan | 260/243 C |
|---|---|---|---|
| 3,701,775 | 10/1972 | Berges et al. | 260/243 C |
| 3,796,801 | 3/1974 | Guarini | 424/246 |
| 3,813,391 | 5/1974 | Naito et al. | 260/243 C |
| 3,814,775 | 6/1974 | Naito et al. | 260/243 C |
| 3,819,623 | 6/1974 | Takano et al. | 260/243 C |
| 3,883,520 | 5/1975 | De Marinis | 260/243 C |
| 3,907,786 | 9/1975 | Naito et al. | 260/243 C |
| 3,928,336 | 12/1975 | Essery et al. | 260/243 C |
| 3,931,160 | 1/1976 | Dunn | 260/243 C |
| 3,946,000 | 5/1976 | Naito et al. | 260/243 C |

OTHER PUBLICATIONS

Farmdoc Abstract 22850w.
Farmdoc Abstract 18330x.

*Primary Examiner*—Alton D. Rollins
*Attorney, Agent, or Firm*—Herbert W. Taylor, Jr.

[57] ABSTRACT

7-(D-α-Hydroxy-2-arylacetamido)-3-(2-carboxyalkyl-2,3-dihydro-s-triazolo[4,3-b]pyridazin-3-on-6-ylthiomethyl)-3-cephem-4-carboxylic acids and derivatives containing blocking groups on the α-hydroxy group and their nontoxic, pharmaceutically acceptable salts are valuable as antibacterial agents and are particularly valuable as therapeutic agents in poultry and in animals, including man, in the treatment of infectious diseases caused by many Gram-positive and Gram-negative bacteria. A preferred compound is 7-(D-mandelamido)-3-(2-carboxyalkyl-2,3-dihydro-s-triazolo[4,3-b]pyridazin-3-on-6-ylthiomethyl)-3-cephem-4-carboxylic acid.

45 Claims, No Drawings

7-(D-α-HYDROXY-2-ARYLACETAMIDO)-3-(2-CARBOXYALKYL-2,3-DIHYDRO-s-TRIAZOLO-[4,3-b]PYRIDAZIN-3-ON-6-YLTHIOMETHYL)-3-CEPHEM-4-CARBOXYLIC ACIDS AND DERIVATIVES

CROSS-REFERENCE TO RELATED APPLICATION

This application is a continuation-in-part of our prior, copending application Ser. No. 705,226 filed July 13, 1976, now abandoned.

BACKGROUND OF THE INVENTION

1. Field of the Invention

The cephalosporins of the present invention possess the usual attributes of such compounds and are particularly useful in the treatment of bacterial infections by parenteral administration.

2. Description of the Prior Art

Early issued disclosures of 3-thiolated cephalosporins in which the 7-substituent is 7-mandelamido (7-α-hydroxyphenylacetamido) are found, for example, in U.S. Pat. No. 3,641,021, Farmdoc 60837U, U.S. Pat. No. 3,796,801, Great Britain Pat. No. 1,328,340 (Farmdoc 38983T), U.S. Pat. No. 3,701,775, Japan Kokai No. 4844293 (Farmdoc 55334U) and in Hoover et al., J. Med. Chem. 17(1), 34–41 (1974) and Wick et al., Antimicrobial Ag. Chemo., 1(3), 221–234 (1972).

Later such compounds are described in U.S. Pat. Nos. 3,812,116, 3,814,754, 3,821,207, 3,840,531, 3,855,213, 3,868,369, 3,884,914, 3,903,278, 3,910,900, 3,928,334, 3,928,335, 3,928,336, 3,928,337, 3,928,592, 3,933,808, 3,946,005, 3,950,330 and 3,957,768 and U.S. published patent application Ser. No. B 473,040.

U.S. Pat. No. 3,819,623 (and, for example, also U.K. Pat. No. 1,295,841 and West Germany Pat. No. 1,953,861) discloses specifically and with working details the preparation of 2-mercapto-1,3,4-thiadiazole-5-acetic acid and its conversion to 7-(1H-tetrazol-1-ylacetamido)-3-(5-carboxymethyl-1,3,4-thiadiazol-2-ylthiomethyl)-3-cephem-4-carboxylic acid which is also disclosed in West Germany Offenlegungsschrift No. 2,262,262.

U.S. Pat. Nos. 3,883,520 and 3,931,160 and Farmdoc Abstract 22850W make reference to 3-heterocyclicthiomethyl cephalosporins containing a number of substituents (including carboxyl) on the numerous heterocycles included but these references are completely general in nature and include no physical constants, yields, methods of synthesis or the like and do not even name any such compound containing a carboxyl substituent.

U.S. Pat. No. 3,928,336 provides a review of much of the older cephalosporin art.

U.S. Pat. Nos. 3,813,391, 3,814,755, 3,907,786 and 3,946,000 disclose cephalosporins containing various fused ring bicyclic thiols.

Farmdoc abstract 18830X discloses compounds of the formula

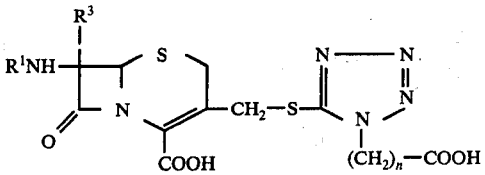

(where $R^1$ = acyl or H; $R^3$ = H or methoxy; $n$ = 1–9).

SUMMARY OF THE INVENTION

This invention comprises the acids having the D configuration in the 7-sidechain and the formula

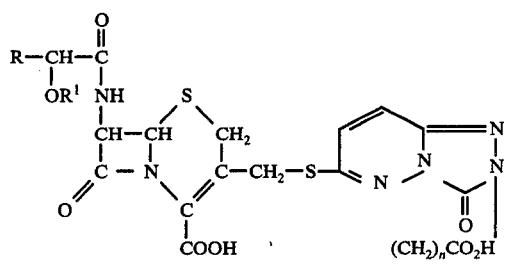

wherein $n$ is one or two and $R^1$ is hydrogen or formyl and R is

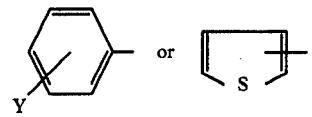

and Y is hydrogen, chlorine, bromine, fluorine, trifluoromethyl, amino, nitro, hydroxy, lower-alkyl of 1–4 carbon atoms or lower alkoxy of 1–4 carbon atoms and the nontoxic, pharmaceutically acceptable salts of those acids and the easily hydrolyzed esters of those acids including especially the pivaloyloxymethyl, acetoxymethyl, acetonyl, phenacyl and methoxymethyl esters and the silyl esters such as the trimethylsilyl ester.

In the preferred embodiments of this invention R is 2-thienyl, 3-thienyl, phenyl, chlorophenyl, bromophenyl, trifluoromethylphenyl, tolyl or methoxyphenyl.

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)-alkylpiperidine, e.g. N-ethylpiperidine, and other amines which have been used to form salts with benzyl-penicillin.

Particularly preferred embodiments of this invention comprises the acids having the D configuration in the 7-sidechain and the formula

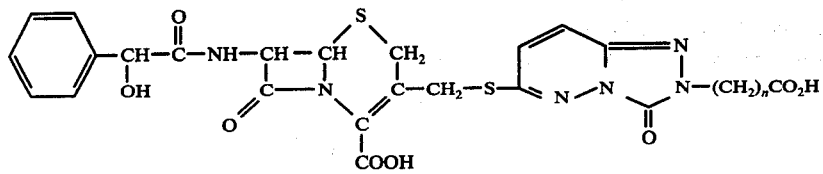

wherein n is one or two and their nontoxic, pharmaceutically acceptable salts and easily hydrolyzed esters.

Also included in this invention are the compounds

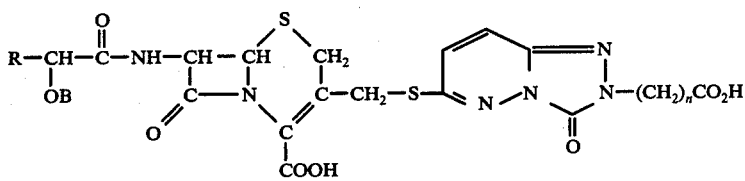

(used as either intermediates or metabolic precursors) in which the α-hydroxy group is "blocked" by substituents such as dichloroacetyl (U.K. Pat. Nos. 962,024 and 1,328,340), formyl (U.S. Pat. No. 3,641,021), trimethylsilyl or tetrahydropyranyl (U.K. Pat. No. 1,328,340).

There is also provided, according to the present invention, the process for the preparation of a compound having the formula

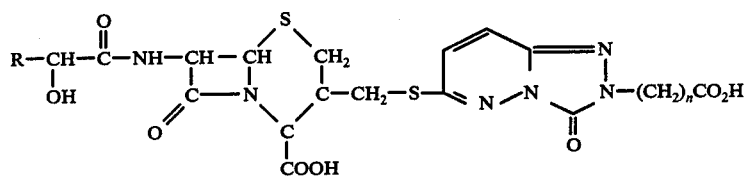

wherein n is one or two and R is as defined above and the nontoxic salts and easily hydrolyzed esters thereof which comprises reacting a compound of the formula

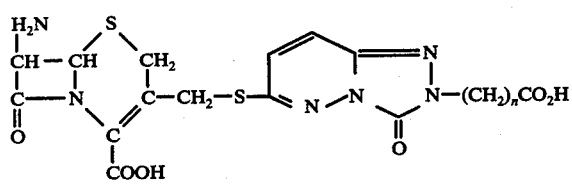

wherein n is one or two or a salt or easily hydrolyzed ester or Schiff base (as with benzaldehyde) thereof with an acylating derivative of the acid (in which the hydroxy group may be protected) having the formula

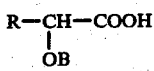

wherein R is as defined above and wherein B represents hydrogen or the protecting group (that is, with that acid or its reactive derivative substituted at the carboxyl group) to produce a compound (in which the hydroxyl group may be protected) having the formula wherein n is one or two or the corresponding salt or easily hydrolyzed ester thereof wherein B represents hydrogen or the protecting group, and if such a protecting group is present subsequently if desired subjecting the resulting compound to chemical removal of the protecting group, that is, subjecting the resulting compound to elimination reaction of the protecting group.

The compounds of the present invention are prepared according to the present invention by coupling with a particular 3-thiolated-7-aminocephalosporanic acid designated II, that is, 7-amino-3-(2-carboxymethyl or 2-carboxyethyl-2,3-dihydro-s-triazolo[4,3-b]pyridazin-3-on-6-ylthiomethyl)-3-cephem-4-carboxylic acid or a salt or easily hydrolyzed ester or Schiff base as with benzaldehyde thereof (including but not limited to those of U.S. Pat. No. 3,284,451 and U.K. Pat. No. 1,229,453 and any of the silyl esters described in U.S. Pat. No. 3,249,622 for use with 7-aminopenicillanic acid and used in Great Britain Pat. No. 1,073,530 and particularly the pivaloyloxymethyl, acetoxymethyl, methoxymethyl, acetonyl, phenacyl, p-nitrobenzyl and β,β,β-trichloroethyl esters) D-mandelic acid or a substituted D-mandelic acid as described herein or their functional equivalent as an acylating agent for a primary amino group. After coupling, any hydroxy blocking group present is removed to give the desired product.

One process of the present invention stated more specifically is the process for the preparation of a product having the D-configuration in the sidechain and the formula

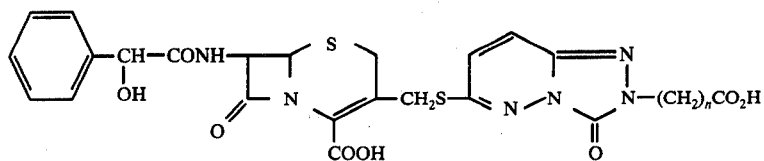

wherein n is one or two or a salt thereof which comprises the consecutive steps of a. preparing an acylating derivative of D-mandelic acid having the formula

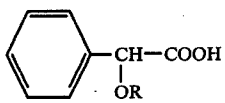

wherein the hydroxyl blocking group R represents dichloroacetyl, silyl and preferably trimethylsilyl, tetrahydropyranyl or, preferably, formyl in an anhydrous organic solvent such as benzene, ethanol or preferably tetrahydrofuran, at room temperature or below and preferably at about 5° C;

b. mixing therewith, preferably slowly, a solution at about the same temperature in a solvent, preferably aqueous tetrahydrofuran, containing substantially the same number of moles of a tertiary amine, preferably a tertiary alkylamine such as triethylamine and substantially the same number of moles of 7-amino-3-(2-carboxymethyl or 2-carboxyethyl-2,3-dihydro-s-triazolo[4,3-b]-pyridazin-3-on-6-ylthiomethyl)-3-cephem-4-carboxylic acid or a salt or an easily hydrolyzed Schiff base, as with benzaldehyde, thereof to produce the intermediate acid having the formula

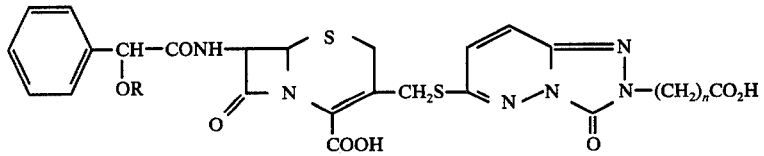

wherein n is one or two or a salt thereof wherein R has the meaning set out above; and c. removing said hydroxyl blocking group R by conventional chemical methods to produce said product or salt thereof.

In preferred embodiments of the present invention R represents formyl which is removed in step C by treatment with aqueous alkali such as aqueous sodium bicarbonate or R represents dichloroacetyl which is removed in step C by alkaline hydrolysis, preferably at about pH 9-10, or R represents trimethylsilyl which is removed in step C by exposure to aqueous acid.

Other compounds of the present invention are made in like manner.

Thus, with respect to said substituted or unsubstituted D-mandelic acid to be used to couple with compound II, functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. A particularly useful anhydride is D-mandelic acid carboxyanhydride (U.S. Pat. No. 3,167,549) or the corresponding substituted D-mandelic acid carboxyanhydride. In addition, an acid azide or an active ester or thioester (e.g., with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain 1,008,170 and Novak and Weichet, Experientia XXI, 6, 360 (1965)] or by the use of enzymes or of an N,N'-carbonyldiimidazole or an N,N'-carbonylditriazole [cf. South African patent specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew. Chem. International Edition 3, 582, (1964)] or of an isoxazolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203-6205 (1972)] or of diethylphosphoryl cyanide [DEPC; Tetrahedron Letters No. 18, pp. 1595-1598 (1973)] or of diphenyl phosphite [Tetrahedron Letters No. 49, pp. 5047-5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

For the coupling of the substituted or unsubstituted D-mandelic acid (with or without a protecting group on the α-hydroxyl) as described above with compound II (or a salt or preferably an easily hydrolyzed ester or Schiff base, as with benzaldehyde, thereof) it is also convenient and efficient to utilize as the coupling agent N-ethoxycarbonyl-2-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a substituted or unsubstituted D-mandelamido-cephalosporanic acid (in which the α-hydroxy group is protected or unprotected and so is the carboxyl group) with 2-carboxymethyl-or 2-carboxyethyl-2,3-dihydro-6-mercapto-s-triazolo[4,3-b]pyridazin-3-one and then removing the protecting group if any is present on the α-hydroxy group or on the carboxyl group or both. The displacement of such an acetoxy group with such a thiol is a well-known reaction and may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. Such substituted or unsubstituted D-mandelamido-cephalosporanic acids are prepared by the procedures described generally or specifically in *J. Med. Chem.* 17(1), 34–41 (1974) and the references cited therein.

In the treatment of bacterial infections in man, the compounds of this invention are administered parenterally, in accordance with conventional procedures for antibiotic administration, in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excipients. The dosage units are preferably in the form of liquid preparations such as solutions or suspensions.

STARTING MATERIALS

6-Chloro-2-(2-cyanoethyl)-2,3-dihydro-s-triazolo[4,3-b]pyridazin-3-on.

To a solution of 6-chloro-2,3-dihydro-s-triazolo[4,3-b]pyridazin-3-on [P. Francabilla and F. Lauria, J. Het. Chem. 8, 415 (1971)] (17 g., 0.1 mole) in dry DMF (300 ml.) was added potassium tert.-butoxide (0.5 g., 4.5 m.moles) with stirring. Acrylonitrile (6.6 g., 0.12 mole) in dry DMF (10 ml.) was added to the mixture. The mixture was stirred at 100°–110° C. for 24 hours, then poured into water (700 ml.) and extracted with ethyl acetate (5 × 400 ml.). The organic extracts were combined, dried over $Na_2SO_4$ and evaporated. The residue was crystallized from ethyl acetate to give light yellow needles of 6-chloro-2-(2-cyanoethyl)-2,3-dihydro-s-triazolo[4,3-b]pyridazin-3-on (2.5 g., 11%). M.p. 166°–168° C.

ir: $\nu_{max}^{KBr}$ 2230, 1720, 1550, 1500 $cm^{-1}$.

uv: $\lambda_{max}^{dioxane}$ 373 nm (ε 2000).

nmr: $\delta_{ppm}^{DMSO-d_6}$ 3,03 (2H, t, J=6.0 Hz, $CH_2$), 4.21 (2H, t, J=6.0 Hz, $CH_2$), 7.23 (1H, d, J=10.0 Hz, pyridazine-H), 7.93 (1H, d, J=10.0 Hz, pyridazine-H).

Anal. Calc'd. for $C_8H_6N_5OCl$: C, 42.97; H, 2.70; N, 31.32; Cl, 15.86. Found: C, 42.73; 42.56; H, 2.57, 2.50; N, 31.36, 31.68; Cl, 15.96, 15.81.

2-(2-Carboxyethyl)-6-chloro-2,3-dihydro-s-triazolo[4,3-b]pyridazin-3-on.

A solution of 6-chloro-2-(2-cyanoethyl)-2,3-dihydro-s-triazolo[4,3-b]pyridazin-3-on (724 mg.) in 6N-HCl (15 ml.) was refluxed for 6 hours. The reaction mixture was extracted with ethyl acetate (10 × 20 ml.). The combined extracts were washed with saturated aqueous sodium chloride (50 ml.), dried over $Na_2SO_4$ and evaporated to give light yellow, solid 2-(2-carboxyethyl)-6-chloro-2,3-dihydro-s-triazolo[4,3-b]-pyridazin-3-on (567 mg., 72%). M.p. >170° C. (sublimation).

ir: $\nu_{max}^{KBr}$ 3400–2400, 1730, 1710, 1540 $cm^{-1}$.

uv: $\lambda_{max}^{dioxane}$ 377 nm (ε 1500).

nmr: $\delta_{ppm}^{D_2O+NaHCO_3}$ 2.70 (2H, t, J=7.0 Hz, $CH_2$), 4.24 (2H, t, J=7.0 Hz, $CH_2$), 7.17 (1H, d, J=10.0 Hz, pyridazine-H), 7.70 (1H, d, J=10.0 Hz, pyridazine-H).

Anal. Calc'd for $C_8H_7N_4O_3Cl$: C, 39.60; H, 2.91; N, 23.09; Cl, 14.61. Found: C, 39.62, 39.48; H, 2.97. 2.67; N, 23.05, 22.70; Cl, 13.93, 14.12.

2-(2-Carboxyethyl)-2,3-dihydro-6-mercapto-s-triazolo[4,3-b]pyridazin-3-on.

A mixture of 2-(2-carboxyethyl)-6-chloro-2,3-dihydro-s-triazolo[4,3-b]pyridazin-3-on (567 mg., 2.34 m.moles) and 70% sodium hydrosulfide dihydrate (924 mg., 7.02 m.mole) in water (10 ml.) was stirred at room temperature for two hours. The reaction mixture was adjusted successively to pH 1 with c. HCl, to pH 10 with NaOH and then to pH 1 with c. HCl. The rsulting precipitate of 2-(carboxyethyl)-2,3-dihydro-6-mercapto-s-triazolo[4,3-b]pyridazin-3-on was collected by filtration and washed with water. Yield: 418 mg. (74%). M.p. 174°–176° C.

ir: $\nu_{max}^{KBr}$ 3600–2600, 2440, 1730, 1720 (sh) $cm^{-1}$.

uv: $\lambda_{max}^{pH\ 7\ buffer}$ 262 nm (ε 17000), 318 nm (ε 6600).

nmr: $\delta_{ppm}^{DMSO-d_6}$ 2.73 (2H, t, J=7.0 Hz, $CH_2$), 4.07 (2H, t, J=7.0 Hz, $CH_2$), 7.30 (1H, d, J=10.0 Hz, pyridazine-H), 7.74 (1H, d, J=10.0 Hz, pyridazine-H).

Anal. Calc'd. for $C_8H_8N_4O_3S$: C, 40.00; H, 3.36; N, 23.32; S, 13.35. Found: C, 39.08, 39.06; H, 3.12, 3.20; N, 22.65, 22.70; S, 14.23, 14.29.

7-Amino-3-[2-(2-carboxyethyl)-2,3-dihydro-s-triazolo[4,3-b]pyridazin-3-on-6-ylthiomethyl]-3-cephem-4-carboxylic Acid.

A mixture of 7-ACA (405 mg., 1.49 m.moles), the thiol 2-(2-carboxyethyl)-2,3-dihydro-6-mercapto-s-triazolo[4,3-b]pyridazin-3-on (357 mg., 1.49 m.moles) and $NaHCO_3$ (375 mg., 4.47 m.moles) in 0.1 M phosphate buffer (pH 7, 8 ml.) was stirred at 80° C. for 30 minutes. The reaction mixture was cooled and filtered to remove insolubles. The filtrate was adjusted to pH 1–2 with c. HCl. The resulting precipitate, 7-amino-3-[2-(2-carboxyethyl)-2,3-dihydro-s-triazolo[4,3-b]pyridazin-3-on-6-ylthiomethyl]-3-cephem-4-carboxylic acid, was collected by filtration and washed with water. Yield: 519 mg. (77%).

ir: $\nu_{max}^{KBr}$ 3600–2200, 1800, 1725, 1620, 1550, 1480 cm$^{-1}$.

uv: $\lambda_{max}^{pH\ 7\ buffer}$ 253 nm ($\epsilon$ 20000), 298 nm ($\epsilon$ 10000).

nmr: $\delta_{ppm}^{D_2O+K_2CO_3}$ 2.20 (2H, t, J=7.0 Hz, C$\underline{H}_2$), 3.40 (1H, d, J=17.5 Hz, 2-H), 3.85 (1H, d, J=17.5 Hz, 2-H), 4.00–4.50 (4H, m, 3-C$\underline{H}_2$ and N-C$\underline{H}_2$-), 5.01 (1H, d, J=4.0 Hz, 6-H), 5.40 (1H, d, J=4.0 Hz, 7-H), 6.94 (1H, d, J=10.0 Hz, pyridazine-H), 7.44 (1H, d, J=10.0 Hz, pyridazine-H).

Anal. Calc'd. for $C_{16}H_{16}N_6O_6S_2 \cdot 3/2H_2O$: C, 40.09; H, 3.99; N, 17.52; S, 13.37. Found: C, 40.06, 40.12; H, 3.33, 3.34; N, 16.96, 16.98; S, 13.87, 13.98.

7-ACA refers to 7-aminocephalosporanic acid and DMF to dimethylformamide.

Scheme 1. Preparation of
7-Amino-3-(2-carboxymethyl-2,3-dihydro-s-triazolo[4,3-b]pyridazin-3-on-6-ylthiomethyl)-3-cephem-4-carboxylic Acid.

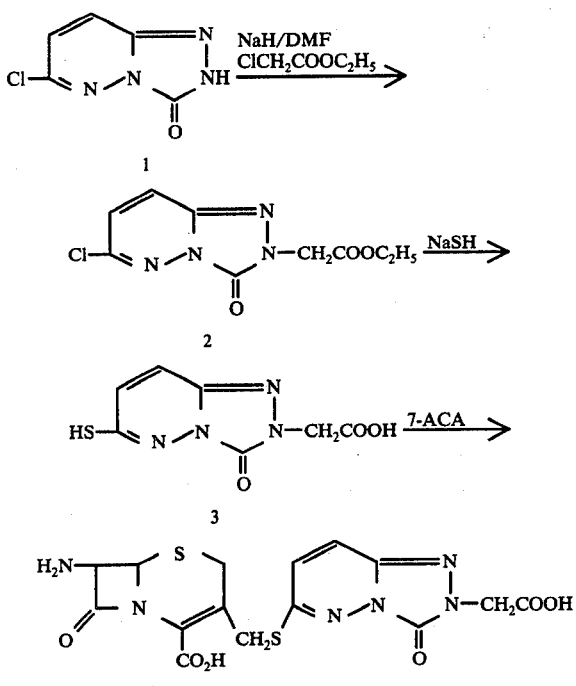

6-Chloro-2,3-dihydro-2-ethoxycarbonylmethyl-s-triazolo[4,3-b]pyridazin-3-one (2)

To a solution of 6-chloro-2,3-dihydro-s-triazolo[4,3-b]pyridazin-3-one [P. Francavilla and F. Lauria, J. Het. Chem., 8, 415 (1971)] (1, 1.00 g., 5.9 m.mole) in dry DMF (30 ml.) was added sodium hydride (50% in paraffin, 0.3 g., 6.3 m.mole) under stirring with formation of yellow crystals. To the mixture was added ethyl chloroacetate (1.4 ml., 13 m.mole) and the mixture was heated at 90° C. for 8 hours with stirring. After cooling, the reaction mixture was poured into water (50 ml.) and extracted with toluene (5 × 40 ml.). The organic extracts were combined, dried over anhydrous sodium sulfate and evaporated at reduced pressure. The residue was crystallized with benzene-n-hexane to give yellow needles of 2 (1.16 g., 77%), m.p. 114°–115° C. (lit. 110° C.).

ir: $\nu_{max}^{KBr}$ 1735, 1710 cm$^{-1}$.

uv: $\lambda_{max}^{EtOH}$ 231 nm ($\epsilon$, 26000).

nmr: $\delta_{ppm}^{CDCl_3}$ 7.58 (1H, d, J=10 Hz, pyridazine-H), 6.98 (1H, d, J=10 Hz, pyridazine-H), 4.80 (2H, s, -C$\underline{H}_2$CO), 4.27 (2H, q, J=7.5 Hz, C$\underline{H}_2$CH$_3$), 1.29 (3H, t, J=7.5 Hz, CH$_2$C$\underline{H}_3$).

Anal. Calc'd. for $C_9H_9N_4O_3Cl$: C, 42.12; H, 3.53; N, 21.83; Cl, 13.81. Found: C, 41.54, 41.46; H, 3.22, 3.49; N, 21.51, 21.53; Cl, 13.88, 13.99.

2-Carboxymethyl-2,3-dihydro-6-mercapto-s-triazolo[4,3-b]pyridazin-3-one (3)

To a solution of 6-chloro-2,3-dihydro-2-ethoxycarbonylmethyl-s-triazolo[4,3-b]pyridazin-3-one (2, 30 g., 0.12 mole) in ethanol (900 ml.) was added NaSH.2H$_2$O (70% pure, 45.9 g., 0.36 mole) and the mixture was refluxed for 0.5 hour. The reaction mixture was evaporated at reduced pressure. The residue was dissolved in water (200 ml.) and concentrated HCl was added to the solution to adjust to pH 2. The precipitate (3) was collected by filtration and washed with water. Yield 18.3 g. (69%).

ir: $\nu_{max}^{KBr}$ 2900, 2450, 1750, 1660 cm$^{-1}$.

uv: $\lambda_{max}^{1\%NaHCO_3aq.}$ 260 nm ($\epsilon$, 19500), 313 nm ($\epsilon$, 7000).

nmr: $\delta_{ppm}^{DMSO-d_6}$ 7.88 (1H, d, J=10 Hz, pyridazine-H), 7.45 (1H, d, J=10 Hz, pyridazine-H), 4.72 (2H, s, C$\underline{H}_2$CO).

Anal. Calc'd. for $C_7H_6N_4O_3S$: C, 37.17; H, 2.67; N, 24.77; S, 14.17. Found: C, 37.35, 37.23; H, 2.26, 2.28; N, 23.58, 23.69; S, 14.32.

7-Amino-3-(2-carboxymethyl-2,3-dihydro-s-triazolo[4,3-b]pyridazin-3-on-6-ylthiomethyl)-3-cephem-4-carboxylic Acid (4)

To a suspension of 7-aminocephalosporanic acid (8.79 g., 32.2 m.mole) in 0.1 M phosphate buffer (pH 7, 149 ml.) were added NaHCO$_3$ (8.14 g., 97.0 m.mole) and the thiol 3 (7.30 g., 32.2 m.mole) with stirring. The mixture was heated at 80° C. for 0.5 hour under N$_2$ stream. The mixture was treated with active carbon and adjusted to pH 3 with concentrated HCl. The resulting precipitate was collected by filtration and washed with water to give 7.59 g. (54%) of 4.

ir: $\nu_{max}^{KBr}$ 1800, 1720, 1600, 1540, 1470 cm$^{-1}$.

uv: $\lambda_{max}^{Buffer}$ (pH 7) 252 nm ($\epsilon$, 19500), 298 nm ($\epsilon$, 8400).

nmr: $\delta_{ppm}^{D_2O+K_2CO_3}$ 7.56 (1H, d, J=9 Hz, pyridazine-H), 7.05 (1H, d, J=9 Hz, pyridazine-H), 5.45 (1H, d, J=5 Hz, 6-H), 5.05 (1H, d, 5 Hz, 7-H), 4.43 (1H, d, J=14 Hz, 3-CH$_2$), 4.04 (1H, d, J=14 Hz, 3-CH$_2$), 3.88 (1H, d, J=18 Hz, 2-H), 3.45 (1H, d, J=18 Hz, 2-H).

Pivaloyloxymethyl-7-amino-3-(2-carboxymethyl-2,3-dihydro-s-triazolo[4,3-b]pyridazin-3-on-6-ylthiomethyl)-3-cephem-4-carboxylate.

Method A

The title compound is produced by substituting for the 7-aminocephalosporanic acid used immediately above an equimolar weight of pivaloyloxymethyl 7-aminocephalosporanate hydrochloride prepared according to Example 2 of U.K. Pat. No. 1,229,453 from 7-aminocephalosporanic acid. German 1,904,585 (Farmdoc 39,445) is equivalent to U.K. Pat. No. 1,229,453.

Method B

The title compound is produced by substituting for the 0.025 mole (6.8 g.) 7-aminocephalosporanic acid used in the procedure of Example 2 of U.K. Pat. No. 1,229,453 an equimolar weight of 7-amino-3-(2-carboxymethyl-2,3-dihydro-s-triazolo[4,3-b]pyridazin-3-on-6-ylthiomethyl)-3-cephem-4-carboxylic acid (4).

The respective acetoxymethyl, methoxymethyl, acetonyl and phenacyl esters of 7-amino-3-(2-carboxymethyl-2,3-dihydro-s-triazolo[4,3-b]pyridazin-3-on-6-ylthiomethyl)-3-cephem-4-carboxylic acid are prepared by substituting in Method B above chloromethyl pivalate used therein an equimolar weight of chloromethyl acetate, chloromethyl methyl ether, chloroacetone and phenacyl bromide, respectively.

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group and the first three are also of interest because on oral administration they may provide different rates and amounts of absorption and may give differing concentrations of the active antibacterial agent in blood and tissues.

These five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767-773 (1971). In another good method the triethylamine salt of 7-aminocephalosporanic acid is reacted directly with the active halogen compound, as in U.K. Pat. No. 1,229,453.

These esters of 7-aminocephalosporanic acid are then reacted with the nucleophile 2-carboxymethyl-2,3-dihydro-6-mercapto-s-triazolo[4,3-b]pyridazin-3-one in the same manner as is illustrated herein for 7-aminocephalosporanic acid itself. The 3-thiolated ester of 7-aminocephalosporanic acid is then coupled with the substituted or unsubstituted D-mandelic acid. Before or after removal of any blocking group on the αhydroxy group of the 7-sidechain, the ester of the cephalosporin so obtained is, if not used per se, converted to its free acid, including if desired, any salt by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006-2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

Preparation of D-mandelic acid carboxyanhydride

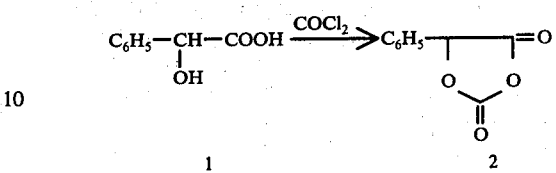

D-Mandelic acid carboxyanhydride (2)

Phosgene was bubbled through a solution of 2.0 g. (0.013 mole) of D(−)-mandelic acid (1) in dry tetrahydrofuran for 30 minutes. The solution was allowed to stand overnight after which time it was heated under reflux for 10 minutes. Evaporation of the solvent under reduced pressure afforded an oily residue which was solidified by trituration with n-hexane (20 ml.). The product was collected by filtration and dried in vacuo on KOH. Yield 2.3 g. of D-mandelic acid carboxyanhydride.

IR: $\nu_{max}^{nuj}$ 1895, 1875, 1780 cm$^{-1}$.

The preferred and most active compounds of the present invention are those having the D configuration at the α-carbon atom in the 7-sidechain, that is, those made from D-mandelic acid or a monosubstituted D-mandelic acid as illustrated herein. In addition, the configuration at the two optically active, asymmetric centers in the β-lactam nucleus is that found in cephalosporin C produced by fermentation and in the 7-aminocephalosporanic acid derived therefrom.

The following examples are given in illustration of, but not in limitation of, the present invention. All temperatures are in degrees Centigrade. 7-Aminocephalosporanic acid is abbreviated as 7-ACA; -ACA- represents the moiety having the structure

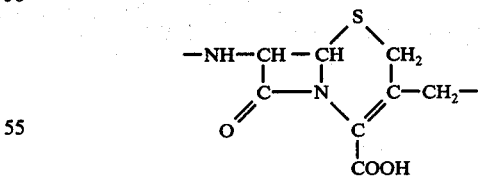

and thus 7-ACA can be represented as

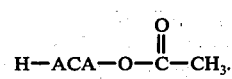

Methyl isobutyl ketone is represented as MIBK. "Skellysolve B" is a petroleum ether fraction of B.P. 60°-68° C. consisting essentially of n-hexane.

DESCRIPTION OF THE PREFERRED EMBODIMENTS

EXAMPLE 1

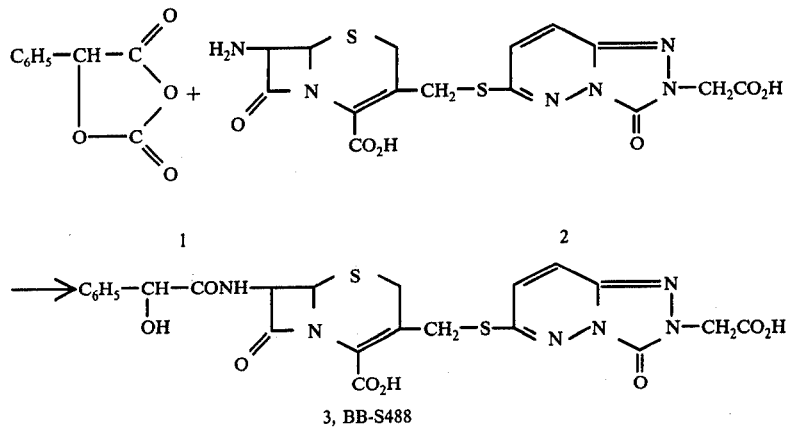

BB-S488;
7-(D-Mandelamido)-3-(2-carboxymethyl-2,3-dihydro-s-triazolo[4,3-b]pyridazin-3-on-6-ylthiomethyl)-3-cephem-4-carboxylic Acid (3)

D-(−)-Mandelic acid O-carboxyanhydride (U.S. Pat. Nos. 3,167,549, 3,840,531 and 3,910,900), (1, 400 mg., 2.3 m. mole) was added portionwise to a solution of 7-amino-3-(2-carboxymethyl-2,3-dihydro-s-triazolo[4,3-b]pyridazin-3-on-6-ylthiomethyl)-3-cephem-4-carboxylic acid (2, 657 mg., 1.5 m. mole) and sodium bicarbonate (445 mg., 5.3 m. mole) in 50% aqueous acetone (30 ml.) at ca 0° C. with vigorous stirring. The mixture was stirred for 1 hour at room temperature and evaporated under reduced pressure below 40° C. to remove acetone. The resulting aqueous solution was washed with ether and acidified to pH 1 with dilute HCl to afford a gummy precipitate, which was collected by filtration, washed with water and dissolved in tetrahydrofuran (THF) (100 ml.). The THF solution was treated with a small amount of active carbon, dried over anhydrous sodium sulfate and filtered. The filtrate was evaporated under reduced pressure and the residue was triturated with ether. The pale yellow precipitate was collected by filtration and chromatographed on a silica gel column (Wako-gel C-200, 10 g.) eluted with a solution of chloroform-methanol (20:1). The fractions containing the desired product were combined and concentrated under reduced pressure. The concentrate was diluted with ether (100 ml.) to precipitate the product (3), which was collected by filtration, washed with ether (30 ml.) and dried. Yield 279 mg. (34%). M.p. 173°–176° C. (dec.).

ir: $\nu_{max}^{KBr}$ 3600–2400, 1770, 1720, 1520, 1495, 1365, 1245 cm$^{-1}$.

uv: $\lambda_{max}^{EtOH}$ 254 nm ($\epsilon$ 18000), 297 nm ($\epsilon$ 9000, sh).

nmr: $\delta_{ppm}^{DMSO-d_6}$ 3.68 (2H, m, 2-H), 4.03 (1H, d, J=13 Hz, 3-H), 4.34 (1H, d, J=13 Hz, 3-H), 4.64 (2H, s, NCH$_2$CO), 5.00 (1H, d, J=4 Hz, 6-H), 5.02 (1H, s, PhCH), 5.63 (1H, d-d, J=4 & 9 Hz, a doublet with addition of D$_2$O, J=4 Hz, 7-H), 6.97 (1H, d, J=10 Hz, pyridazine-H), 7.1–7.4 (5H, m, phenyl-H), 7.60 (1H, d, J=10 Hz, pyridazine-H), 8.60 (1H, d, J=9 Hz, disappeared with addition of D$_2$O, CONH).

Anal. Calc'd. for $C_{23}H_{20}N_6O_8S_2 \cdot \frac{1}{2}H_2O$: C, 47.50; H, 3.64; N, 14.45; S, 11.03. Found: C, 47.34; H, 3.48; N, 13.90; S, 11.01.

In vitro activity (Table 1)

The MIC's were determined by the Steers' agar dilution method using Mueller-Hinton agar against 4 gram-positive and 28 gram-negative bacteria and the results are shown in Table 1.

In vitro activity (Tables 2 and 3)

MIC determinations were performed by serial two-fold agar dilution method using Steers' apparatus on Mueller-Hinton agar plate against 51-gram-positive and 95 gram-negative bacteria. The results are shown in Tables 2 and 3.

Media effect on MIC

The MIC's were determined by using three kinds of agar media [Nutrient (NA), Mueller-Hinton (MHA) and Heart-Infusion (HIA)]. The results obtained with BB-S488 and cefamandole are shown in Table 4, which indicates little media effect in these cephalosporins.

Blood levels in mice

Groups of mice were administered subcutaneously graded doses of 40, 20 and 10 mg./kg.. The blood samples collected from orbital sinuses were assayed by the paper disc-agar diffusion method on *Sarcina lutea* PCI 1001 plates. The results are shown in Table 5.

In vivo activity

Comparative in vivo evaluation was made by the standard experimental infection in mice against the following pathogenic bacteria:

*S. aureus* Smith
*E. coli* Juhl
*K. pneumoniae* A9977

The results are shown in Table 6.

Table 1

The in vitro Antibacterial Activity of BB-S488 By Agar Dilution Method (Mueller-Hinton Agar).

| Test Organism | | MIC (mcg./ml.) | |
| --- | --- | --- | --- |
| | | BB-S488 | Cefamandole |
| S. aureus Smith | A9537 | 0.2 | 0.05 |
| S. aureus | A9497 | 0.1 | 0.05 |
| S. aureus BX-1633 | A9606 | 0.4 | 0.1 |
| St. faecalis | A9536 | 100 | 50 |
| E. coli NIHJ | | 0.025 | 0.025 |
| E. coli ATCC 8739 | | 0.1 | 0.05 |
| E. coli Juhl | A15119 | 0.2 | 0.4 |

Table 1-continued

The in vitro Antibacterial Activity of BB-S488
By Agar Dilution Method (Mueller-Hinton Agar).

| Test Organism | | MIC (mcg./ml.) BB-S488 | Cefamandole |
|---|---|---|---|
| E. coli BX-1373 | | 0.2 | 0.8 |
| E. coli | A15810 | 0.1 | 0.4 |
| E. coli | A9660 | 0.05 | 0.1 |
| E. coli | A15147 | 3.1 | 0.4 |
| Kl. pneumoniae | A9678 | 3.1 | 3.1 |
| Kl. pneumoniae | A9977 | 0.05 | 0.2 |
| Kl. pneumoniae | A15130 | 0.2 | 0.8 |
| Kl. pneumoniae | A9867 | 0.2 | 0.8 |
| Pr. vulgaris | A9436 | 0.1 | 0.4 |
| Pr. vulgaris | A9699 | 0.2 | 6.3 |
| Pr. mirabilis | A9554 | 0.05 | 0.4 |
| Pr. mirabilis | A9900 | 0.1 | 0.8 |
| Pr. morganii | A9553 | >100 | >100 |
| Pr. morganii | A20031 | 0.1 | 0.8 |
| Pr. rettgeri | A15167 | 0.05 | 0.2 |
| Ps. aeruginosa | A9930 | >100 | >100 |
| Ps. aeruginosa | A9843 | >100 | >100 |
| Shig. dysenteriae | | 0.025 | 0.1 |
| Shig. flexneri | A9684 | 12.5 | 6.3 |
| Shig. sonnei | A9516 | 0.025 | 0.05 |
| Serr. marcescens | A20019 | 100 | 100 |
| Enterob. cloacae | A9656 | 3.1 | 3.1 |
| Sal. enteritidis | A9531 | 0.05 | 0.1 |
| Sal. typhosa | A9498 | 0.05 | 0.1 |
| Sal. anthracis | A9504 | 0.1 | 0.1 |

Table 2

In vitro Antibacterial Activity in Mueller-Hinton Agar (Gram-positive)

| Code No. | Test Organism | MIC (mcg./ml.) BB-S488 | Cefamandole |
|---|---|---|---|
| Sa-2 | S. aureus Smith A9537 | 0.4 | 0.2 |
| Sa-3 | S. aureus No. 193 | 0.8 | 0.2 |
| Sa-8 | S. aureus | 0.4 | 0.2 |
| Sa-9 | S. aureus No. 193 | 0.8 | 0.2 |
| Sa-10 | S. aureus A20239 | 1.6 | 0.4 |
| Sa-11 | S. aureus BX-1633 A9606 | 0.4 | 0.2 |
| Sa-12 | S. aureus A9497 | 0.2 | 0.1 |
| Sa-29 | S. aureus No. 193 | 1.6 | 0.8 |
| Sa-33 | S. aureus Terajima | 0.0125 | 0.0125 |
| Sa-34 | S. aureus A15092 | 0.8 | 0.2 |
| Sa-35 | S. aureus A15094 | 0.8 | 0.4 |
| Sa-36 | S. aureus Russell | 0.8 | 0.4 |
| Sa-37 | S. aureus A9524 | 1.6 | 0.8 |
| Sa-38 | S. aureus A9534 | 0.4 | 0.2 |
| Sa-39 | S. aureus A9578 | 0.8 | 0.4 |
| Sa-40 | S. aureus A9601 | 0.8 | 0.4 |
| Sa-41 | S. aureus A9602 | 0.8 | 0.2 |
| Sa-44 | S. aureus A15097 | 25 | 25 |
| Sa-56 | S. aureus A9630 | 3.1 | 0.8 |
| Sa-57 | S. aureus A9748 | 25 | 3.1 |
| Sa-58 | S. aureus A15033 | 12.5 | 1.6 |
| Sa-59 | S. aureus A15096 | 100 | 6.3 |
| Sa-60 | S. aureus A20604 | 50 | 3.1 |
| Sa-61 | S. aureus A20605 | 100 | 6.3 |
| Sa-62 | S. aureus A20606 | 3.1 | 0.8 |
| Sa-63 | S. aureus A20607 | >100 | 12.5 |
| Sa-64 | S. aureus A20608 | 100 | 6.3 |
| Sa-65 | S. aureus A20609 | 100 | 6.3 |
| Sa-66 | S. aureus A20610 | 100 | 6.3 |
| Sa-67 | S. aureus A20611 | 100 | 6.3 |
| Sa-68 | S. aureus A20612 | 1.6 | 0.4 |
| Sa-69 | S. aureus A20613 | 100 | 6.3 |
| Sp-1 | S. pyogenes S-23 | 0.4 | 0.1 |
| Sp-2 | S. pyogenes Dick | 0.4 | 0.1 |
| Sp-3 | S. pyogenes A9604 | 0.4 | 0.1 |
| Sp-4 | S. pyogenes A20065 | 0.2 | 0.1 |
| Sp-5 | S. pyogenes A15040 | 0.4 | 0.1 |
| Sp-6 | S. pyogenes A20066 | 0.4 | 0.1 |
| Sp-7 | S. pyogenes Dig 7 | 0.4 | 0.1 |
| Sp-8 | S. pyogenes A15041 | 0.4 | 0.1 |
| Sp-9 | S. pyogenes A20201 | 0.4 | 0.1 |
| Sp-10 | S. pyogenes A20202 | 0.4 | 0.1 |
| Dp-1 | D. pneumoniae Type II | 0.2 | 0.2 |
| Dp-2 | D. pneumoniae Type I Neufeld | 0.2 | 0.2 |
| Dp-3 | D. pneumoniae Type III | 0.2 | 0.2 |
| Dp-4 | D. pneumoniae A9585 | 0.2 | 0.2 |
| Dp-5 | D. pneumoniae A15069 | 0.2 | 0.2 |
| Dp-6 | D. pneumoniae A20167 | 0.2 | 0.2 |
| Dp-7 | D. pneumoniae A20759 | 0.2 | 0.2 |
| Dp-8 | D. pneumoniae A20769 | 0.2 | 0.2 |

Table 2-continued

In vitro Antibacterial Activity in Mueller-Hinton Agar (Gram-positive)

| Code No. | Test Organism | MIC (mcg./ml.) BB-S488 | Cefamandole |
|---|---|---|---|
| Dp-9 | D. pneumoniae A20770 | 0.2 | 0.2 |

Table 3

In vitro Antibacterial Activity in Mueller-Hinton Agar (Gram-negative)

| Code No. | Test Organism | MIC (mcg./ml.) BB-S488 | Cefamandole |
|---|---|---|---|
| Ec-1 | E. coli NIHJ | 0.2 | 0.1 |
| Ec-3 | E. coli Juhl A15119 | 0.2 | 0.8 |
| Ec-4 | E. coli A15169 | 12.5 | 6.3 |
| Ec-5 | E. coli K-12, ML-1630 A20363 | 0.2 | 0.8 |
| Ec-11 | E. coli A20366 | 50 | 25 |
| Ec-15 | E. coli ATCC 8739 | 0.2 | 0.1 |
| Ec-34 | E. coli A9660 | 0.1 | 0.1 |
| Ec-35 | E. coli A9435 | 0.4 | 0.8 |
| Ec-36 | E. coli A15147 | 3.1 | 1.6 |
| Ec-40 | E. coli A20361 | 0.2 | 0.8 |
| Ec-44 | E. coli A9535 | 0.1 | 0.1 |
| Ec-45 | E. coli A15148 | 3.1 | 1.6 |
| Ec-46 | E. coli A15164 | 25 | 12.5 |
| Ec-47 | E. coli A15170 | 100 | 50 |
| Ec-49 | E. coli A20107 | 0.4 | 0.2 |
| Ec-50 | E. coli A20109 | 0.2 | 0.8 |
| Ec-51 | E. coli A20343 | 50 | 12.5 |
| Ec-56 | E. coli A20365 | 25 | 12.5 |
| Ec-58 | E. coli A9675 | 0.4 | 1.6 |
| Ec-59 | E. coli A20766 | 0.2 | 0.8 |
| Ec-62 | E. coli A20895 | 0.4 | 0.8 |
| El-1 | E. cloacae A9656 | 3.1 | 3.1 |
| El-2 | E. cloacae A20364 | 3.1 | 3.1 |
| El-4 | E. cloacae A20650 | 1.6 | 1.6 |
| El-6 | E. cloacae A9657 | 0.8 | 0.8 |
| El-7 | E. cloacae A9659 | 1.6 | 0.8 |
| El-8 | E. cloacae A9655 | 1.6 | 1.6 |
| El-9 | E. cloacae A20021 | >100 | 100 |
| El-11 | E. cloacae A20344 | >100 | >100 |
| El-12 | E. cloacae A21006 | 1.6 | 3.1 |
| El-14 | E. cloacae A20953 | 0.8 | 3.1 |
| Pm-1 | P. mirabilis A9554 | 0.1 | 0.8 |
| Pm-2 | P. mirabilis A9900 | 0.2 | 1.6 |
| Pm-3 | P. mirabilis A20119 | 0.4 | 3.1 |
| Pm-4 | P. mirabilis A20454 | 0.2 | 1.6 |
| Pm-5 | P. mirabilis A9702 | 0.1 | 0.8 |
| Pm-6 | P. mirabilis A21222 | 1.6 | 1.6 |
| Pg-1 | P. morganii A9553 | >100 | >100 |
| Pg-2 | P. morganii A20031 | 0.2 | 1.6 |
| Pg-3 | P. morganii A9636 | 0.8 | 1.6 |
| Pg-5 | P. morganii A15166 | 0.1 | 0.2 |
| Pg-6 | P. morganii A20455 | 0.4 | 1.6 |
| Pg-7 | P. morganii A20457 | 0.2 | 0.8 |
| Pg-8 | P. morganii A15153 | 0.1 | 0.8 |
| Pg-9 | P. morganii A15149 | 0.8 | 3.1 |
| Pv-1 | P. vulgaris A9436 | 0.2 | 0.8 |
| Pv-2 | P. vulgaris A9526 | 6.3 | 1.6 |
| Pv-3 | P. vulgaris A9699 | 6.3 | 50 |
| Pv-4 | P. vulgaris ATCC 9920 | 0.1 | 0.2 |
| Pv-5 | P. vulgaris A9539 | 25 | >100 |
| Pv-6 | P. vulgaris A9716 | 0.1 | 0.8 |
| Pv-7 | P. vulgaris A21240 | 25 | >100 |
| Pr-1 | P. rettgeri A15167 | 0.1 | 0.2 |
| Pr-2 | p. rettgeri A9637 | 0.1 | 0.1 |
| Pr-4 | P. rettgeri A20645 | 0.1 | 0.1 |
| Pr-5 | P. rettgeri A20915 | 0.2 | 0.8 |
| Pr-6 | P. rettgeri A20920 | 0.1 | 0.2 |
| Pn-1 | P. inconstans A20615 | 0.1 | 0.8 |
| Ps-1 | P. stuartii A20745 | 0.4 | 0.8 |
| Ps-2 | P. stuartii A20894 | 0.2 | 0.8 |
| Ps-3 | P. stuartii A20911 | 0.8 | 0.8 |
| Ps-4 | P. stuartii A21051 | 50 | 25 |
| Ps-5 | P. stuartii A21057 | 0.2 | 0.8 |
| Kp-1 | K. pneumoniae D11 | 0.1 | 0.8 |
| Kp-2 | K. pneumoniae A9678 | 3.1 | 1.6 |
| Kp-3 | K. pneumoniae A9977 | 0.1 | 0.8 |
| Kp-4 | K. pneumoniae A15130 | 0.2 | 0.8 |
| Kp-7 | K. pneumoniae A9867 | 0.4 | 0.8 |
| Kp-8 | K. pneumoniae A20680 | 25 | 12.5 |
| Kp-9 | K. pneumoniae A20636 | 12.5 | 12.5 |
| Kp-10 | K. pneumoniae A20328 | 6.3 | 3.1 |
| Kp-11 | K. pneumoniae A20330 | 1.6 | 12.5 |
| Kp-12 | K. pneumoniae A21228 | 6.3 | 6.3 |
| Kx-2 | Klebsiella sp. A9662 | 0.4 | 1.6 |

Table 3-continued
In vitro Antibacterial Activity in Mueller-Hinton Agar (Gram-negative)

| Code No. | Test Organism | MIC (mcg./ml.) BB-S488 | Cefamandole |
|---|---|---|---|
| Kx-3 | Klebsiella sp. A20346 | 0.2 | 0.8 |
| Sm-1 | S. marcescens A20019 | 25 | 25 |
| Sm-2 | S. marcescens A20335 | 3.1 | 12.5 |
| Sm-3 | S. marcescens A20336 | 6.3 | 12.5 |
| Sm-4 | S. marcescens A20442 | 6.3 | 12.5 |
| Sm-5 | S. marcescens A20222 | 3.1 | 12.5 |
| Sm-6 | S. marcescens A20460 | 6.3 | 12.5 |
| Sm-9 | S. marcescens A20333 | 6.3 | 50 |
| Sm-10 | S. marcescens A20334 | 6.3 | 50 |
| Sm-11 | S. marcescens A20459 | 6.3 | 25 |
| Sm-12 | S. marcescens A20461 | 6.3 | 50 |
| Se-1 | S. enteritidis A9531 | 0.1 | 0.2 |
| St-1 | S. typhosa | 0.1 | 0.2 |
| Sh-1 | S. paratyphi | 0.1 | 0.2 |
| St-101 | S. typhimurium | 0.1 | 0.2 |
| Sd-1 | S. dysenteriae | 0.1 | 0.2 |
| Sr-1 | S. flexneri A9684 | 12.5 | 3.1 |
| Ss-1 | S. sonnei Yale | 0.1 | 0.1 |
| Cx-1 | Citrobacter sp. A20673 | 1.6 | 1.6 |
| Cx-2 | Citrobacter sp. A20694 | 1.6 | 1.6 |
| Cx-3 | Citrobacter sp. A20695 | 1.6 | 1.6 |

Table 6
In vivo Activity

| Test Organism | Dose | BB-S488 | Cefamandole |
|---|---|---|---|
| S. aureus Smith | 25 mg./kg. | 5/5* | 5/5 |
| | 6.3 | 5/5 | 5/5 |
| | 1.6 | 5/5 | 5/5 |
| | 0.4 | 5/5 | 1/5 |
| | 0.1 | 2/5 | |
| | $PD_{50}$ | 0.12 mg./kg. | 0.6 mg./kg. |
| E. coli Juhl | 25 mg./kg. | 5/5 | 5/5 |
| | 6.3 | 5/5 | 5/5 |
| | 1.6 | 5/5 | 2/5 |
| | 0.4 | 5/5 | 0/5 |
| | 0.1 | 2/5 | |
| | $PD_{50}$ | 0.12 mg./kg. | 1.8 mg./kg. |
| K. pneumoniae | 25 mg./kg. | 5/5 | 5/5 |
| | 6.3 | 5/5 | 1/5 |
| | 1.6 | 5/5 | 0/5 |
| | 0.4 | 4/5 | 0/5 |
| | 0.1 | 0/5 | |
| | $PD_{50}$ | 0.26 mg./kg. | 6.25 mg./kg. |

| Test Organism | Run No. | No. of $LD_{50}$ | Dose (mg./kg.) | BB-S488 | Cefamandole |
|---|---|---|---|---|---|
| E. cloacae A20464 (El-19) | C-811 | 1 × 10 | 100 | 5/5 | 5/5 |
| | | | 25 | 5/5 | 55/ |
| | | | 6.3 | 5/5 | 5/5 |
| | | | 1.6 | 4/5 | 4/5 |
| | | | 0.4 | 2/5 | 1/5 |
| | | | $PD_{50}$ (mg./kg.) | 0.54 | 0.8 |

Table 4
Media Effect on MIC of BB-S488 and Reference Compounds

| Code No. | Test Organism | BB-S488 NA | BB-S488 HIA | BB-S488 MHA | Cefamandole NA | Cefamandole HIA | Cefamandole MHA |
|---|---|---|---|---|---|---|---|
| Sa-2 | S. aureus Smith A9537 | 0.8 | 0.8 | 0.8 | 0.2 | 0.2 | 0.2 |
| Sa-11 | S. aureus BX-1633 A9606* | 3.1 | 1.6 | 0.8 | 0.4 | 0.4 | 0.4 |
| Sa-44 | S. aureus A15097 | >100 | >100 | 100 | 6.3 | 3.1 | 3.1 |
| Sf-3 | S. faecalis A9536 | >100 | >100 | >100 | >100 | 100 | 100 |
| Ec-1 | E. coli NIHJ | 0.1 | 0.05 | 0.05 | 0.1 | 0.1 | 0.05 |
| Ec-3 | E. coli Juhl A15119 | 0.2 | 0.4 | 0.2 | 0.2 | 0.4 | 0.4 |
| Ec-11 | E. coli A20366* | >100 | >100 | >100 | 50 | 25 | 50 |
| Ec-15 | E. coli ATCC 8739 | 0.1 | 0.2 | 0.2 | 0.1 | 0.1 | 0.1 |
| Ec-36 | E. coli A15147* | 6.3 | 6.3 | 6.3 | 1.6 | 3.1 | 3.1 |
| Ec-46 | E. coli A15164* | 50 | >100 | 100 | 25 | 12.5 | 12.5 |
| Ec-51 | E. coli A20343* | 50 | >100 | >100 | 12.5 | 25 | 25 |
| El-1 | E. cloacae A9656 | 12.5 | 6.3 | 3.1 | 6.3 | 3.1 | 3.1 |
| El-2 | E. cloacae A20364* | 12.5 | 6.3 | 3.1 | 6.3 | 100 | 50 |
| El-11 | E. cloacae A20344* | >100 | >100 | >100 | >100 | >100 | >100 |
| Kp-3 | K. pneumoniae A9977 | 0.4 | 0.2 | 0.2 | 0.4 | 0.8 | 0.8 |
| Kp-4 | K. pneumoniae A15130 | 0.8 | 0.8 | 0.4 | 0.8 | 0.8 | 0.8 |
| Kx-3 | Klebsiella sp. A20346* | 0.2 | 0.2 | 0.2 | 0.4 | 0.4 | 0.4 |
| Pv-1 | P. vulgaris A9436 | 0.2 | 0.2 | 0.1 | 0.2 | 0.4 | 0.4 |
| Pv-3 | P. vulgaris A9699* | 0.8 | 100 | 0.8 | 6.3 | 100 | 50 |
| Pm-1 | P. mirabilis A9554 | 0.1 | 0.1 | 0.1 | 0.2 | 0.4 | 0.8 |
| Pm-2 | P. mirabilis A9900 | 0.1 | 0.2 | 0.2 | 0.4 | 0.4 | 0.8 |
| Pg-1 | P. morganii A9553* | >100 | >100 | >100 | >100 | >100 | >100 |
| Pg-2 | P. morganii A20031 | 0.2 | 0.2 | 0.1 | 0.4 | 0.8 | 0.8 |
| Pg-6 | P. morganii A20455* | 0.4 | 0.8 | 0.4 | 1.6 | 3.1 | 1.6 |
| Pr-1 | P. rettgeri A15167 | 0.4 | 0.1 | 0.05 | 0.2 | 0.1 | 0.2 |
| Ps-1 | P. stuartii A20745 | 50 | 50 | 12.5 | 6.3 | 6.3 | 1.6 |
| Ps-2 | P. stuartii A20894 | 0.8 | 0.4 | 0.2 | 0.4 | 0.4 | 0.2 |
| Ps-3 | P. stuartii A20911* | 50 | 25 | 12.5 | 6.3 | 6.3 | 3.1 |
| Sm-1 | S. marcescens A20019* | >100 | >100 | >100 | 50 | 50 | 100 |
| Sm-3 | S. marcescens A20336 | 100 | >100 | 0.8 | 50 | 50 | 100 |
| Pa-3 | P. aeruginosa A9930 | 100 | >100 | >100 | >100 | >100 | >100 |
| Ba-3 | B. anthracis A9504 | 0.4 | 0.2 | 0.2 | 0.4 | 0.2 | 0.4 |

*β-lactamase +

Table 5
Subcutaneous Mice Blood Levels

| Dose | Time | BB-S488 Mcg./Ml. | Cefamandole Mcg./Ml. |
|---|---|---|---|
| 40 mg./kg. | 15' | 19 | 18 |
| | 30' | 17 | 11 |
| | 60' | 12 | 3.9 |
| | 120' | 1.6 | 0.3 |
| 20 mg./kg. | 15' | 7.4 | 9.5 |
| | 30' | 6 | 4.1 |
| | 60' | 4.3 | 1 |
| | 120' | 0.7 | <0.1 |
| 10 mg./kg. | 15' | 5 | 3.8 |
| | 30' | 3 | 1.5 |
| | 60' | 0.8 | 0.3 |
| | 120' | — | 0.1 |

Urinary Recovery in Rats

| Dose (sc) | % Recovery (0–24 Hrs.) BB-S488 | Cefamandole |
|---|---|---|
| 10 mg./kg. | 38.8 | 58.3 |

No. of survivors/No. tested

Nephrotoxicity Test in Rabbits

No nephrotoxic sign was seen in the rabbits treated with 100 mg./kg. (iv) of BB-S488 while cephaloridine showed severe nephrotoxicity in the comparative test.

Additional PD$_{50}$ Data (Single sc Treatment)

| Test Organism | Run No. | No. of LD$_{50}$ | Dose (mg./kg.) | BB-S 488 | Cefamandole |
|---|---|---|---|---|---|
| K. pneumoniae | C-805 | 3×10³ | 25 | 5/5 | 5/5 |
| | | | 6.3 | 5/5 | 1/5 |
| | | | 1.6 | 5/5 | 0/5 |
| | | | 0.4 | 4/5 | 0/5 |
| | | | 0.1 | 0/5 | — |
| | | | PD$_{50}$ (mg./kg.) | 0.26 | 9.4 |
| P. vulgaris A9436 (Pv-1) | C-808 | 1×10 | 50 | — | 3/5 |
| | | | 25 | 5/5 | — |
| | | | 12.5 | — | 1/5 |
| | | | 6.3 | 5/5 | — |
| | | | 3.1 | — | 0/5 |
| | | | 1.6 | 3/5 | — |
| | | | 0.8 | — | 0/5 |
| | | | 0.4 | 1/5 | — |
| | | | PD$_{50}$ (mg./kg.) | 1.1 | 36 |
| P. mirabilis A9900 (Pm-2) | C-810 | 1×10³ | 50 | — | 2/5 |
| | | | 25 | 5/5 | — |
| | | | 12.5 | — | 1/5 |
| | | | 6.3 | 5/5 | — |
| | | | 3.1 | — | 0/5 |
| | | | 1.6 | 4/5 | — |
| | | | 0.8 | — | 0/5 |
| | | | 0.4 | 0/5 | — |
| | | | 0.2 | — | 0/5 |
| | | | 0.1 | 0/5 | — |
| | | | PD$_{50}$ (mg./kg.) | 1.1 | 50 |

Stability of BB-S488

Stability of BB-S488 was determined in both a 10% and an 0.02% solution. The stability is indicated as the relative activity remaining in the test solution at given periods to the initial solution. The activity was assayed using paper discs on *B. subtilis* PCI 219 plate (pH 6).

(1) Stability in a 10% Aqueous Solution at Room Temperature

| Compound | pH$^{(1)}$ | Remaining Activity (%) | | | |
|---|---|---|---|---|---|
| | | 0 | 2 | 3 | 7 Days |
| BB-S488 | 6.1 | 100 | 128 | 90 | 116 |

| Compound | pH$^{(2)}$ | Remaining Activity (%) | | | | |
|---|---|---|---|---|---|---|
| | | 0 | 1 | 2 | 3 | 7 Days |
| BB-S488 | 4 | 100 | | 93 | 78 | 102 |
| | 7 | 100 | | 87 | 64 | 56 |
| | 9 | 100 | 20 | 14 | 13 | 0 |

$^{(1)}$Unadjusted pH of the 10% solution.
$^{(2)}$pH 4: 0.1 M AcOH - NaOAc buffer.
pH 7: 0.1 M phosphate buffer.
pH 9: 0.1 M NH$_4$OH—NH$_4$Cl buffer.

EXAMPLE 2

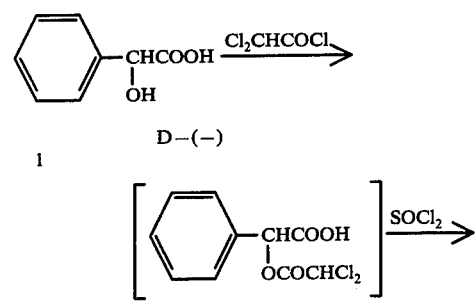

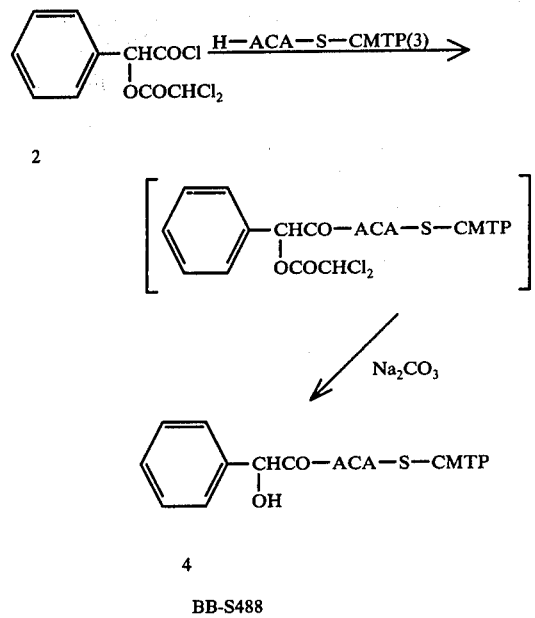

BB-S488

Dichloroacetylmandeloyl Chloride (2)

A mixture of D(-)-mandelic acid (1, 1.52 g., 10 m.mole) and dichloroacetyl chloride (4.41 g., 30 m.mole) was heated at 80°-85° C. for 1.5 hrs. and the excess dichloroacetyl chloride was removed under diminished pressure. To the residue was added thionyl chloride (2.5 ml.) and the mixture was heated under reflux for 1.5 hrs. Excess thionyl chloride was removed by distillation and dry benzene was added. Evaporation was repeated. The residual oil was kept over KOH at 1 mm Hg overnight at room temperature to remove dichloroacetyl chloride. Yield, 2.8 g. (100%). This product was used in the next step without further purification.

ir: $\nu_{max}^{liq.}$ 1780, 1160 cm$^{-1}$.
nmr: $\delta_{ppm}^{CCl_4}$ 5.91 (1H, s, PhCH or COCHCl$_2$), 6.00 (1H, s, PhCH or COCHCl$_2$), 7.32 (5H, s, phenyl-H).

BB-S488; 7-(D-Mandelamido)-3-(2-carboxymethyl-2,3-dihydro-s-triazolo[4,3-b]pyridazin-3-on-6-ylthiomethyl)-3-cephem-4-carboxylic Acid. (4)

A solution of the above-obtained dichloroacetylmandeloyl chloride (2, 2.8 g., 10 m.mole) in dry acetone (30 ml.) was added dropwise to a stirred solution of 7-amino-3-(2-carboxymethyl-2,3-dihydro-s-triazolo[4,3-b]-pyridazin-3-on-6-ylthiomethyl)-3-cephem-4-carboxylic acid (H-ACA-S-CMTP) (3, 3.94 g., 9 m.mole) and triethylamine (3.54 g., 35 m.mole) in 50% aqueous acetone (120 ml.) at 0°-5° C. The mixture was allowed to rise to room temperature during 1 hour with stirring and was adjusted to pH 11 with 5% aqueous sodium carbonate (ca 12 ml. was required). The mixture was allowed to stand at room temperature for 30 minutes, acidified to pH 1 with dilute HCl and evaporated under reduced pressure to remove acetone below 40° C. The precipitate was collected by filtration, washed with water (20 ml.) and air-dried. The dried material was dissolved in THF (150 ml.), stirred for 5 minutes at 40°-50° C. and filtered to remove insoluble unreacted 3 (0.54 g., 14% recovery). The filtrate was chromatographed on a silica gel column (Wakogel, C-200, 30 g.) and eluted with chloroform-methanol (100:5). The eluates were collected in 50 ml. fractions monitoring by tlc (silica gel, solvent, $CH_3CN$-water = 4:1, detected with $I_2$). The fractions containing the desired product were combined, treated with a small amount of carbon and evaporated under reduced pressure. The residue was triturated with chloroform (50 ml.) to yield, 2.36 g. (46%) of 7-(D-mandelamido)-3-(2-carboxymethyl-2,3-dihydro-s-triazolo[4,3-b]pyridazin-3-on-6-ylthiomethyl)-3-cephem-4-carboxylic acid (4). M.P., 165°–170° C. (dec.).

ir: $\nu_{max}^{KBr}$ 3600–2500, 1780, 1720, 1500, 1410, 1355, 1220, 1195 $cm^{-1}$.

uv: $\lambda_{max}^{EtOH}$ 254 nm ($\epsilon$, 18300), 297 nm (sh, $\epsilon$, 9300).

nmr: $\delta_{ppm}^{DMSO-d_6}$ 3.84 (2H, m, 2-$\underline{H}$), 4.17 (2H, d, 13 Hz, 3-$\underline{H}$), 4.50 (1H, d, 13 Hz, 3-$\underline{H}$), 4.82 (2H, s, $NCH_2COO$), 5.20 (1H, d, 4.5 Hz, 6-$\underline{H}$), 5.25 (1H, s, PhCH), 5.87 (1H, d-d, 4.5 & 9 Hz, 7-$\underline{H}$, a doublet (J=4.5 Hz) by addition of $D_2O$), 7.25 (1H, d, 11 Hz, pyridazine-$\underline{H}$), 7.4–7.7 (5H, m, phenyl-$\underline{H}$), 7.90 (1H, d, 11 Hz, pyridazine-$\underline{H}$), 9.0 (1H, d, 9 Hz, 7-CONH, disappear by addition of $D_2O$).

Anal. Calc'd for $C_{23}H_{20}N_6O_8S_2 \cdot \frac{3}{4}CHCl_3$: C, 43.08; H, 3.16; N, 12.69; S, 9.69. Found: C, 43.11, 43.22; H, 2.97, 3.06; N, 12.80, 12.77; S, 9.64.

EXAMPLE 3

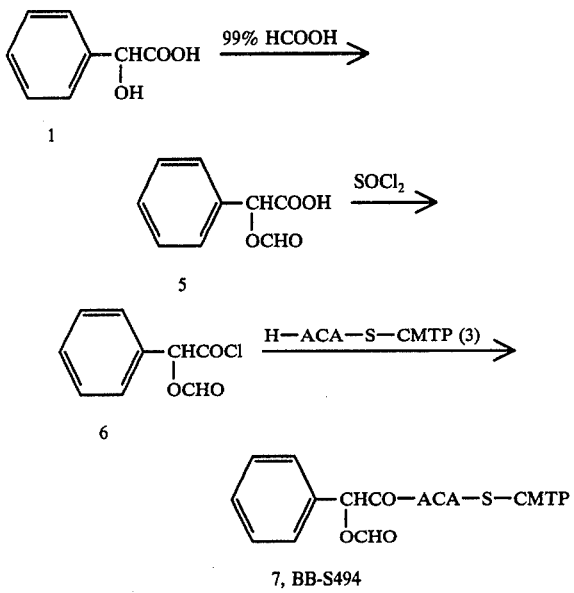

7, BB-S494

O-Formyl-D(-)-mandelic Acid (5)

A mixture of D(-)-mandelic acid (1, 5.0 g., 33 m.mole) and 99% formic acid (80 ml.) was heated at 80°–90° C. for 12 hours. The mixture was evaporated and toluene (100 ml.) was added to the residue and evaporated under reduced pressure to remove formic acid azeotropically. The residue was dissolved in benzene (200 ml.) and the solution was washed with water (2 × 50 ml.). The organic layer was separated, dried with anhydrous sodium sulfate and evaporated under reduced pressure. The residual oil was triturated with cyclohexane (50 ml.) to crystallize. Yield, 3.70 g. (63%) of O-formyl-D(-)-mandelic acid (5) as colorless prisms. M.P., 56°–59° C. (lit. M.P., 55°–58° C.).

ir: $\nu_{max}^{KBr}$ 3400–2800, 1755, 1720, 1160, 990 $cm^{-1}$.

nmr: $\delta_{ppm}^{CDCl_3}$ 5.98 (1H, s, PhCH), 7.31 (5H, m, phenyl-$\underline{H}$), 8.05 (1H, s, OCHO), 10.05 (1H, s, COOH, disappeared by addition of $D_2O$).

O-Formyl-D(-)-mandeloyl Chloride (6)

A mixture of 5 (2.0 g., 11 m.mole) and thionyl chloride (10 ml.) was heated under reflux for 2 hours. Evaporation of the excess thionyl chloride and distillation of the residue under reduced pressure afforded the acid chloride O-formyl-D(-)-mandeloyl chloride (6).

Yield, 1.53 g. (70%). B.P., 120°–122° C./15 mmHg.

ir: $\nu_{max}^{liq.}$ 1805, 1740, 1160, 1140 $cm^{-1}$.

BB-S494;
7-(D-O-Formylmandelamido)-3-(2-carboxymethyl-2,3-dihydro-s-triazolo[4,3-b]pyridazin-3-on-6-ylthiomethyl)-3-cephem-4-carboxylic Acid (7)

A solution of O-formyl-D(-)-mandeloyl chloride (6) (1.0 g., 5.1 m.mole) in dry acetone (10 ml.) was added dropwise to a cold (0° to 5° C.) solution of 7-amino-3-(2-carboxymethyl-2,3-dihydro-s-triazolo[4,3-b]pyridazin-3-on-6-ylthiomethyl)-3-cephem-4-carboxylic acid (3, 1.75 g., 4 m.mole) in 50% aqueous acetone (70 ml.) containing sodium bicarbonate (1.34 g., 16 m.mole). The mixture was stirred for 30 minutes at room temperature and washed with ether. The aqueous layer was acidified to pH 1 with dilute HCl. The separated oily gum was collected and dissolved in THF (100 ml.). The solution was treated with a small amount of carbon and dried with anhydrous sodium sulfate. Evaporation of the solvent under reduced pressure to 10 ml. and dilution with ether afforded the title compound (7) as a pale yellow amorphous powder, 0.91 g. (38%). M.P., 172°–176° C. (dec.).

ir: $\nu_{max}^{KBr}$ 3600–2400, 1775, 1720, 1550, 1355, 1230, 1160 $cm^{-1}$.

uv: $\lambda_{max}^{EtOH}$ 254 nm ($\epsilon$, 20800), 297 nm (sh, $\epsilon$, 10500).

nmr: $\delta_{ppm}^{DMSO-d_6}$ 3.4–4.5 (4H, m, 2-$\underline{H}$ and 3-$\underline{H}$), 4.67 (2H, s, $NCH_2COO$), 4.97 (1H, d, 4 Hz, 6-$\underline{H}$), 5.66 (1H, d-d, 4 & 8 Hz, 7-$\underline{H}$), 7.2–7.5 (5H, m, phenyl-H), 7.64 (1H, d, 10 Hz, pyridazine-$\underline{H}$), 8.29 (1H, s, CHO), 9.29 (1H, d, 8 Hz, 7-CONH, disappeared by addition of $D_2O$).

Anal. Calc'd. for $C_{24}H_{20}N_6O_9S_2 \cdot 1H_2O$: C, 46.60; H, 3.58; N, 13.59; S, 10.37. Found: C, 46.70, 47.20; H, 3.25, 3.34; N, 13.37, 13.78; S, 10.84.

EXAMPLE 4

BB-S488;
7-(D-Mandelamido)-3-(2-carboxymethyl-2,3-dihydro-s-triazolo-[4,3-b]pyridazin-3-on-6-ylthiomethyl)-3-cephem-4-carboxylic Acid (4)

A mixture of 7-(D-O-formylmandelamido-3-(2-carboxymethyl-2,3-dihydro-s-triazolo[4,3-b]pyridazin-3-on-6-ylthiomethyl)-3-cephem-4-carboxylic acid (7) (484 mg., 0.81 m.mole) and sodium bicarbonate (748 mg., 8.9 m.mole) in water (4 ml.) was stirred for 4 hours at room temperature, and acidified to pH 1 with dilute HCl. The precipitate (500 mg.) was collected by filtration, washed with water (2 ml.) and chromatographed on silica gel column (Wako-gel, C-200, 5 g.). The column was eluted with chloroform containing increasing methanol (3–5%) as eluent, and the fractions containing the product were combined, treated with a small amount of carbon and evaporated under reduced pressure. The residue was triturated with ether to give 277 mg. of 7-(D-mandelamido)-3-(2-carboxymethyl-2,3- dihydro-s-triazolo[4,3-b]pyridazin-3-on-6-ylthiomethyl)-3-cephem-4-carboxylic acid (BB-S488; 4). The nmr-estimation of this product showed 10% of 7 still remained.

ir: $\nu_{max}^{KBr}$ 3600–2400, 1770, 1720, 1520, 1495, 1365, 1230 cm$^{-1}$.

uv: $\lambda_{max}^{EtOH}$ 254 nm ($\epsilon$, 20000), 297 nm (sh, $\epsilon$, 9600).

EXAMPLE 5

Sodium Salt of BB-S488

Sodium-2-ethylhexanoate (SEH) (4.0 ml., 1 M solution in ethyl acetate) was added to a solution of 7-(D-mandelamido)-3-(2-carboxymethyl-2,3-dihydro-s-triazolo[4,3-b]pyridazin-3-on-6-ylthiomethyl)-3-cephem-4-carboxylic acid (4) (2.25 g., 3.93 m.mole) in THF (200 ml.). The precipitate was collected by filtration, washed with THF (50 ml.) and dried at 60° C./1 mmHg for 3 hours. Yield of sodium 7-(D-mandelamido)-3-(2-carboxymethyl-2,3-dihydro-s-triazolo[4,3-b]pyridazin-3-on-6-ylthiomethyl)-3-cephem-4-carboxylate, 1.96 g. (bio-yield, 97%), M.P., 230°–240° C. (dec.). The pH of the 10% aqueous solution was 3.6.

ir: $\nu_{max}^{KBr}$ 3600–3000, 1765, 1710, 1605, 1390, 1360, 1190, 1080, 1065 cm$^{-1}$.

uv: $\lambda_{max}^{water}$ nm($E_{1cm}^{1\%}$) 252 (357), 310 (sh, 140).

nmr: $\delta_{ppm}^{D_2O}$ 3.43 (1H, d, 19 Hz, 2-$\underline{H}$), 3.87 (1H, d, 19 Hz, 2-$\underline{H}$), 4.15 (1H, d, 14 Hz, 3-$\underline{H}$), 4.53 (1H, d, 14 Hz, 3-$\underline{H}$), 5.16 (1H, d, 4.5 Hz, 6-$\underline{H}$), 5.36 (1H, s, PhCH), 5.73 (1H, d, 4.5 Hz, 7-$\underline{H}$), 7.13 (1H, d, 10 Hz, pyridazine-$\underline{H}$), 7.57 (5H, s, phenyl-$\underline{H}$), 7.69 (1H, d, 10 Hz, pyridazine-$\underline{H}$).

Anal. Calc'd. for $C_{23}H_{19}N_6O_8S_2Na \cdot 5/4H_2O$: C, 44.77; H, 3.51; N, 13.62; S, 10.39. Found: C, 44.93, 44.79; H, 3.31, 3.15; N, 13.41, 13.33; S, 10.19.

EXAMPLE 6

Aqueous 1N sodium hydroxide solution was added dropwise to a suspension of 7-(D-mandelamido)-3-(2-carboxymethyl-2,3-dihydro-s-triazolo[4,3-b]pyridazin-3-on-6-ylthiomethyl)-3-cephem-4-carboxylic acid (4) (3.51 g.) in water (20 ml.) to adjust to pH 6.0. The solution was lyophilized to yield 3.4 g. (bio-yield, 97%) of disodium 7-(D-mandelamido)-3-(2-carboxymethyl-2,3-dihydro-s-triazolo[4,3-b]pyridazin-3-on-6-ylthiomethyl)-3-cephem-4-carboxylylate. M.p., >240° C. (dec.). The pH of the 5% aqueous solution was 5.4.

ir: $\nu_{max}^{KBr}$ 3600–3000, 1760, 1710, 1605, 1390, 1360, 1190, 1080, 1060 cm$^{-1}$.

uv: $\lambda_{max}^{water}$ nm ($E_{1cm}^{1\%}$) 252 (320), 310 (124).

nmr: $\delta_{ppm}^{D_2O}$ 3.43 (1H, d, 19 Hz, 2-$\underline{H}$), 3.90 (1H, d, 19 Hz, 2-$\underline{H}$), 4.15 (1H, d, 14 Hz, 3-$\underline{H}$), 4.53 (1H, d, 14 Hz, 3-$\underline{H}$), 4.75 (2H, s, NCH$_2$CO), 5.22 (1H, d, 4.5 Hz, 6-$\underline{H}$), 5.42 (1H, s, PhCH), 5.73 (1H, d, 4.5 Hz, 7-$\underline{H}$), 7.22 (1H, d, 10 Hz, pyridazine-$\underline{H}$), 7.65 (5H, s, phenyl-$\underline{H}$), 7.77 (1H, d, 10 Hz, pyridazine-$\underline{H}$).

Anal. Calc'd. for $C_{23}H_{18}N_6O_8S_2Na_2 \cdot 3/2H_2O$: C, 42.92; H, 3.29; N, 13.06; S, 9.96. Found: C, 42.90, 43.19; H, 3.06, 3.01; N, 13.04, 13.03; S, 9.97.

EXAMPLE 7

Substitution of the D-mandelic acid carboxyanhydride in the procedure of Example 1 of an equimolar weight of the carboxyanhydrides prepared in similar fashion from the monosubstituted D-mandelic acids D-2-chloro-mandelic acid,
D-3-chloro-mandelic acid,
D-4-chloro-mandelic acid,
D-2-bromo-mandelic acid,
D-3-bromo-mandelic acid,
D-4-bromo-mandelic acid,
D-2-fluoro-mandelic acid,
D-3-fluoro-mandelic acid,
D-4-fluoro-mandelic acid,
D-2-trifluoromethyl-mandelic acid,
D-3-trifluoromethyl-mandelic acid,
D-4-trifluoromethyl-mandelic acid,
D-2-amino-mandelic acid,
D-3-amino-mandelic acid,
D-4-amino-mandelic acid,
D-2-nitro-mandelic acid,
D-3-nitro-mandelic acid,
D-4-nitro-mandelic acid,
D-2-hydroxy-mandelic acid,
D-3-hydroxy-mandelic acid,
D-4-hydroxy-mandelic acid,
D-2-methyl-mandelic acid,
D-3-methyl-mandelic acid,
D-4-methyl-mandelic acid,
D-2-methoxy-mandelic acid,
D-3-methoxy-mandelic acid and
D-4-methoxy-mandelic acid respectively produces
7-(D-2-chloro-mandelamido)-3-(2-carboxymethyl-2,3-dihydro-s-triazolo[4,3-b]pyridazin-3-on-6-ylthiomethyl)-3-cephem-4-carboxylic acid,
7-(D-3-chloro-mandelamido)-3-(2-carboxymethyl-2,3-dihydro-s-triazolo[4,3-b]pyridazin-3-on-6-ylthiomethyl)-3-cephem-4-carboxylic acid,
7-(D-4-chloro-mandelamido)-3-(2-carboxymethyl-2,3-dihydro-s-triazolo[4,3-b]pyridazin-3-on-6-ylthiomethyl)-3-cephem-4-carboxylic acid,
7-(D-2-bromo-mandelamido)-3-(2-carboxymethyl-2,3-dihydro-s-triazolo[4,3-b]pyridazin-3-on-6-ylthiomethyl)-3-cephem-4-carboxylic acid,
7-(D-3-bromo-mandelamido)-3-(2-carboxymethyl-2,3-dihydro-s-triazolo[4,3-b]pyridazin-3-on-6-ylthiomethyl)-3-cephem-4-carboxylic acid,
7-(D-4-bromo-mandelamido)-3-(2-carboxymethyl-2,3-dihydro-s-triazolo[4,3-b]pyridazin-3-on-6-ylthiomethyl)-3-cephem-4-carboxylic acid,
7-(D-2-fluoro-mandelamido)-3-(2-carboxymethyl-2,3-dihydro-s-triazolo[4,3-b]pyridazin-3-on-6-ylthiomethyl)-3-cephem-4-carboxylic acid,
7-(D-3-fluoro-mandelamido)-3-(2-carboxymethyl-2,3-dihydro-s-triazolo[4,3-b]pyridazin-3-on-6-ylthiomethyl)-3-cephem-4-carboxylic acid,
7-(D-4-fluoro-mandelamido)-3-(2-carboxymethyl-2,3-dihydro-s-triazolo[4,3-b]pyridazin-3-on-6-ylthiomethyl)-3-cephem-4-carboxylic acid,
7-(D-2-trifluoromethyl-mandelamido)-3-(2-carboxymethyl-2,3-dihydro-s-triazolo[4,3-b]pyridazin-3-on-6-ylthiomethyl)-3-cephem-4-carboxylic acid,
7-(D-3-trifluoromethyl-mandelamido)-3-(2-carboxymethyl-2,3-dihydro-s-triazolo[4,3-b]pyridazin-3-on-6-ylthiomethyl)-3-cephem-4-carboxylic acid,
7-(D-4-trifluoromethyl-mandelamido)-3-(2-carboxymethyl-2,3-dihydro-s-triazolo[4,3-b]pyridazin-3-on-6-ylthiomethyl)-3-cephem-4-carboxylic acid,
7-(D-2-amino-mandelamido)-3-(2-carboxymethyl-2,3-dihydro-s-triazolo[4,3-b]pyridazin-3-on-6-ylthiomethyl)-3-cephem-4-carboxylic acid,
7-(D-3-amino-mandelamido)-3-(2-carboxymethyl-2,3-dihydro-s-triazolo[4,3-b]pyridazin-3-on-6-ylthiomethyl)-3-cephem-4-carboxylic acid, 7-(D-4-amino-mandelamido)-3-(2-carboxymethyl-2,3-dihydro-s-triazolo[4,3-b]pyridaain-3-on-6-ylthiomethyl)-3-cephem-4-carboxylic acid, 7-(D-2-nitro-mandelamido)-3-(2-carboxymethyl-2,3-dihydro-s-triazolo[4,3-b]pyridazin-3-on-6-ylthiomethyl)-3-cephem-4-carboxylic acid, 7-(D-3-nitro-mandelamido)-3-(2-carboxymethyl-2,3-dihydro-s-triazolo[4,3-b]pyridazin-3-on-6-ylthiomethyl)-3-cephem-4-carboxylic acid, 7-(D-4-nitro-mandelamido)-3-(2-carboxymethyl-2,3-dihydro-s-triazolo[4,3-b]pyridazin-3-on-6-ylthiomethyl)-3-cephem-4-carboxylic acid, 7-(D-2-hydroxy-mandelamido)-3-(2-carboxymethyl-2,3-dihydro-s-triazolo[4,3-b]pyridazin-3-on-6-ylthiomethyl)-3-cephem-4-carboxylic acid, 7-(D-3-hydroxy-mandelamido)-3-(2-carboxymethyl-2,3-dihydro-s-triazolo[4,3-b]pyridazin-3-on-6-ylthiomethyl)-3-cephem-4-carboxylic acid, 7-(D-4-hydroxy-mandelamido)-3-(2-carboxymethyl-2,3-dihydro-s-triazolo[4,3-b]pyridazin-3-on-6-ylthiomethyl)-3-cephem-4-carboxylic acid, 7-(D-2-methyl-mandelamido)-3-(2-carboxymethyl-2,3-dihydro-s-triazolo[4,3-b]pyridazin-3-on-6-ylthiomethyl)-3-cephem-4-carboxylic acid, 7-(D-3-methyl-mandelamido)-3-(2-carboxymethyl-2,3-dihydro-s-triazolo[4,3-b]pyridazin-3-on-6-ylthiomethyl)-3-cephem-4-carboxylic acid, 7-(D-4-methyl-mandelamido)-3-(2-carboxymethyl-2,3-dihydro-s-triazolo[4,3-b]pyridazin-3-on-6-ylthiomethyl)-3-cephem-4-carboxylic acid, 7-(D-2-methoxy-mandelamido)-3-(2-carboxymethyl-2,3-dihydro-s-triazolo[4,3-b]pyridazin-3-on-6-ylthiomethyl)-3-cephem-4-carboxylic acid, 7-(D-3-methoxy-mandelamido)-3-(2-carboxymethyl-2,3-dihydro-s-triazolo[4,3-b]pyridazin-3-on-6-ylthiomethyl)-3-cephem-4-carboxylic acid, and 7-(D-4-methoxy-mandelamido)-3-(2-carboxymethyl-2,3-dihydro-s-triazolo[4,3-b]pyridazin-3-on-6-ylthiomethyl)-3-cephem-4-carboxylic acid, respectively.

EXAMPLE 8

Substitution for the D-mandelic acid carboxyanhydride in the procedure of Example 1 of an equimolar weight of the carboxyanhydride prepared in similar fashion from D-2-thiopheneglycolic acid and D-3-thiopheneglycolic acid respectively produces 7-(D-α-hydroxy-2-thienylacetamido)-3-(2-carboxymethyl-2,3-dihydro-s-triazolo[4,3-b]pyridazin-3-on-6-ylthiomethyl)-3-cephem-4-carboxylic acid and 7-(D-α-hydroxy-3-thienylacetamido)-3-(2-carboxymethyl-2,3-dihydro-s-triazolo[4,3-b]pyridazin-3-on-6-ylthiomethyl-3-cephem-4-carboxylic acid, respectively.

EXAMPLE 9

7-(D-α-Hydroxy-α-phenylacetamido)-3-(2-carboxymethyl-2,3-dihydro-s-triazolo[4,3-b]pyridazin-3-on-6-ylthiomethyl)-3-cephem-4-carboxylic Acid Prepared From 7-D-Mandelamidocephalosporanic Acid.

0.27 Mole of sodium 7-D-mandelamidocephalosporanate is suspended in 1000 ml. of 0.1 M phosphate buffer of pH 6.4 and there is added 0.31 moles of 2-carboxymethyl-2,3-dihydro-6-mercapto-s-triazolo-[4,3-b]pyridazin-3-one. The solution is heated at 55° C. under a nitrogen atmosphere for five hours. After one hour the pH is adjusted to 6.4 by addition of a small amount of 40% $H_3PO_4$. At the end of the five hour heating period the solution is cooled to 23° C. and the pH adjusted to 2 by the addition of 3 N HCl under a layer of ethyl acetate. The product is extracted into ethyl acetate and stirred for 15 min. at 23° C. with 2 g. of ("Darco KB") decolorizing charcoal. The mixture is then filtered through a pad of diatomaceous earth ("Celite") and the ethyl acetate removed from the filtrate under vacuum. The residue is triturated to a solid with diethyl ether, collected by filtration and dried over $P_2O_5$ under vacuum to yield solid 7-(D-α-hydroxy-α-phenylacetamido)-3-(2-carboxymethyl-2,3-dihydro-s-triazolo[4,3-b]pyridazin-3-on-6-ylthiomethyl)-3-cephem-4-carboxylic acid.

EXAMPLE 10

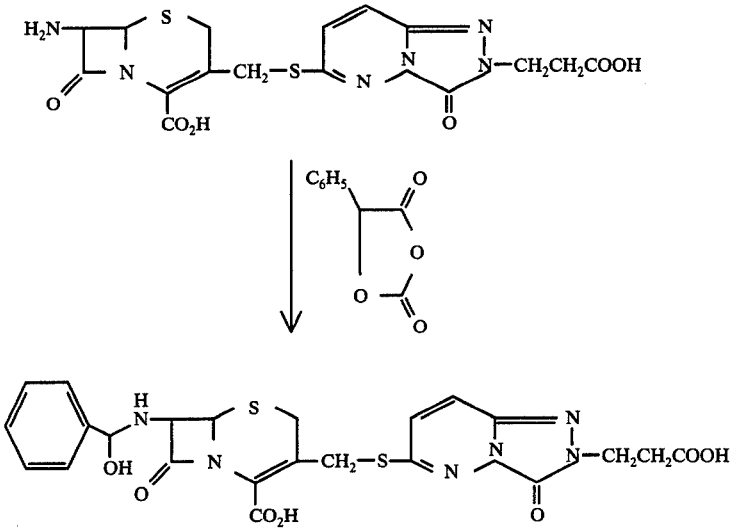

BB-S 527;
7-[D(-)-Mandelamido]-3-[2-(2-carboxyethyl)-2,3-dihydro-s-triazolo-[4,3-b]pyridazin-3-on-6-ylthiomethyl]-3-cephem-4-carboxylic acid To a mixture of 7-amino-3-[2-(2-carboxyethyl)-2,3-dihydro-s-triazolo[4,3-b]pyridazin-3-on-6-ylthiomethyl]-3-cephem-4-carboxylic acid (679 mg, 1.5 m mol) and $NaHCO_3$ (445 mg, 5.3 m mol) in 50% aqueous acetone was added D-(-)-mandelic acid O-carboxyanhydride (400 mg, 2.3 m mol) at 0° C. The mixture was stirred at room temperature for 1 hour and evaporated to remove the organic solvent. The aqueous solution was washed with ether (3 × 10 ml), adjusted to pH 1 with dil. HCl and filtered to collect the crude product, which was dissolved in THF (10 ml), filtered to remove insolubles and evaporated under reduced pressure. The oily residue was triturated with ether. The solid (476 mg) was chromatographed on a column of silica gel (Wako-gle C-200, 10 g) and eluted with MeOH-CHCl$_3$ (MeOH: 0–3%). Fractions which contained the desired product were combined and evaporated to yield 287 Mg (33%) of BB-S 527. M.p. >155° C (dec.).

ir: $\nu_{max}^{KBr}$ 3600 – 2400, 1780, 1720, 1550, 1520 cm$^{-1}$.

uv: $\lambda_{max}^{pH\ 7\ buffer}$ 253 nm ($\epsilon$ 20000), 298 nm ($\epsilon$ 9000).

Anal. Calc'd. for C$_{24}$H$_{22}$N$_6$O$_8$S$_2$.3/2H$_2$O: C, 46.98; H, 4.11; N, 13.70; S, 10.45. Found: C, 47.25, 47.39; H, 3.80, 3.76; N, 12.87, 12.77; S, 10.17.

The sodium salt of BB-S 527

A suspension of the free acid of BB-S 527 (240 mg, 0.4 m mol) in water (5 ml) was adjusted at pH 6.8 with 1 N-NaOH (0.7 ml) to give the clear solution, which was freeze-dried to leave 234 mg (91%, bio-yield) of the sodium salt of BB-S 527 as pale yellow powder. M.p. >210° C (dec.).

ir: $\nu_{max}^{KBr}$ 3600 – 2800, 1770, 1710, 1600 cm$^{-1}$.

uv: $\lambda_{max}^{pH\ 7\ Buffer}$ 253 nm ($\epsilon$ 21000) 298 nm ($\epsilon$ 9300).

Anal. Cald'd. for C$_{24}$H$_{20}$N$_6$O$_8$S$_2$Na$_2$2H$_2$O: C, 43.24; H, 3.63; N, 12.61; S, 9.62. Found: C, 43.39, 43.43; H, 3.20, 3.36; N, 12.63, 12.68; S, 9.42, 9.22.

In vitro antibacterial activity of BB-S 527 compared with BB-S 488 and cefamandole (determined by Steers' agar dilution method on Mueller-Hinton agar plate)

| Organism | MIC (mcg/ml) | | |
|---|---|---|---|
| | BB-S 527 | BB-S 488 | cefamandole |
| S. aureus Smith | 1.6 | 0.8 | 0.2 |
| S. aureus | 0.4 | 0.4 | 0.1 |
| S. aureus BX-1633 | 3.1 | 3.1 | 0.4 |
| St. faecalis | >100 | >100 | >100 |
| E. coli NIHJ | 0.4 | 0.2 | 0.05 |
| E. coli ATCC 8739 | 12.5 | 6.3 | 3.1 |
| E. coli Juhl | 0.4 | 0.2 | 0.8 |
| E. coli BX-1373 | 6.3 | 3.1 | 3.1 |
| E. coli | 0.1 | 0.1 | 0.1 |
| E. coli | 0.1 | 0.05 | 0.1 |
| E. coli | 6.3 | 3.1 | 1.6 |
| Kl. pneumoniae | 6.3 | 3.1 | 3.1 |
| Kl. pneumoniae | 0.2 | 0.1 | 0.8 |
| Kl. pneumoniae | 0.8 | 0.4 | 0.8 |
| Kl. pneumoniae | 0.4 | 0.2 | 0.8 |
| Pr. vulgaris | 0.1 | 0.1 | 0.2 |
| Pr. vulgaris | 12.5 | 0.8 | 50 |
| Pr. mirabilis | 0.2 | 0.05 | 0.8 |
| Pr. mirabilis | 0.1 | 0.05 | 0.2 |
| Pr. morganii | >100 | >100 | >100 |
| Pr. morganii | 0.4 | 0.2 | 0.8 |
| Pr. rettgeri | 0.2 | 0.2 | 0.4 |
| Ps. aeruginosa | >100 | >100 | >100 |
| Ps. aeruginosa | >100 | >100 | >100 |
| Shig. dysenteriae | 0.025 | 0.025 | 0.1 |
| Shig. flexneri | 50 | 25 | 6.3 |
| Shig. sonnei | 0.1 | 0.05 | 0.2 |
| Serr. marcescens | >100 | >100 | 100 |
| Enterob. cloacae | 6.3 | 3.1 | 3.1 |
| Sal. enteritidis | 0.05 | 0.025 | 0.05 |
| Sal. typhosa | 0.1 | 0.05 | 0.1 |
| B. anthracis | 0.4 | 0.2 | 0.4 |

EXAMPLE 11

Substitution for the D-mandelic acid carboxyanhydride in the procedure of Example 10 of an equimolar weight of the carboxyanhydrides prepared in similar fashion from the monosubstituted D-mandelic acids D-2-chloro-mandelic acid,
D-3-chloro-mandelic acid,
D-4-chloro-mandelic acid,
D-2-bromo-mandelic acid,
D-3-bromo-mandelic acid,
D-4-bromo-mandelic acid,
D-2-fluoro-mandelic acid,
D-3-fluoro-mandelic acid,
D-4-fluoro-mandelic acid,
D-2-trifluoromethyl-mandelic acid,
D-3-trifluoromethyl-mandelic acid,
D-4-trifluoromethyl-mandelic acid,
D-2-amino-mandelic acid,
D-3-amino-mandelic acid,
D-4-amino-mandelic acid,
D-2-nitro-mandelic acid,
D-3-nitro-mandelic acid,
D-4-nitro-mandelic acid,
D-2-hydroxy-mandelic acid,
D-3-hydroxy-mandelic acid,
D-4-hydroxy-mandelic acid,
D-2-methyl-mandelic acid,
D-3-methyl-mandelic acid,
D-4-methyl-mandelic acid,
D-2-methoxy-mandelic acid,
D-3-methoxy-mandelic acid and
D-4-methoxy-mandelic acid respectively produces
7-(D-2-chloro-mandelamido)-3-(2-carboxyethyl-2,3-dihydro-s-triazolo[4,3-b]pyridazin-3-on-6-ylthiomethyl)-3-cephem-4-carboxylic acid,
7-(D-3-chloro-mandelamido)-3-(2-carboxyethyl-2,3-dihydro-s-triazolo[4,3-b]pyridazin-3-on-6-ylthiomethyl)-3-cephem-4-carboxylic acid,
7-(D-4-chloro-mandelamido)-3-(2-carboxyethyl-2,3-dihydro-s-triazolo[4,3-b]pyridazin-3-on-6-ylthiomethyl)-3-cephem-4-carboxylic acid,
7-(D-2-bromo-mandelamido)-3-(2-carboxyethyl-2,3-dihydro-s-triazolo[4,3-b]pyridazin-3-on-6-ylthiomethyl)-3-cephem-4-carboxylic acid,
7-(D-3-bromo-mandelamido)-3-(2-carboxyethyl-2,3-dihydro-s-triazolo[4,3-b]pyridazin-3-on-6-ylthiomethyl)-3-cephem-4-carboxylic acid,
7- (D-4-bromo-mandelamido)-3-(2-carboxyethyl-2,3-dihydro-s-triazolo[4,3-b]pyridazin-3-on-6-ylthiomethyl)-3-cephem-4-carboxylic acid,
7-(D-2-fluoro-mandelamido)-3-(2-carboxyethyl-2,3-dihydro-s-triazolo[4,3-b]pyridazin-3-on-6-ylthiomethyl)-3-cephem-4-carboxylic acid,
7-(D-3-fluoro-mandelamido)-3-(2-carboxyethyl-2,3-dihydro-s-triazolo[4,3-b]pyridazin-3-on-6-ylthiomethyl)-3-cephem-4-carboxylic acid,
7-(D-4-fluoro-mandelamido)-3-(2-carboxyethyl-2,3-dihydro-s-triazolo[4,3-b]pyridazin-3-on-6-ylthiomethyl)-3-cephem-4-carboxylic acid,
7-(D-2-trifluoromethyl-mandelamido)-3-(2-carboxyethyl-2,3-dihydro-s-triazolo[4,3-b]pyridazin-3-on-6-ylthiomethyl)-3-cephem-4-carboxylic acid,
7-(D-3-trifluoromethyl-mandelamido)-3-(2-carboxyethyl-2,3-dihydro-s-triazolo[4,3-b]pyridazin-3-on-6-ylthiomethyl)-3-cephem-4-carboxylic acid,
7-(D-4-trifluoromethyl-mandelamido)-3-(2-carboxyethyl-2,3-dihydro-s-triazolo[4,3-b]pyridazin-3-on-6-ylthiomethyl)-3-cephem-4-carboxylic acid,
7-(D-2-amino-mandelamido)-3-(2-carboxyethyl-2,3-dihydro-s-triazolo[4,3-b]pyridazin-3-on-6-ylthiomethyl)-3-cephem-b 4-carboxylic acid, 7-(D-3-amino-mandelamido)-3-(2-carboxyethyl-2,3-dihydro-s-triazolo[4,3-b]pyridazin-3-on-6-ylthiomethyl)-3-cephem-4-carboxylic acid, 7-(D-4-amino-mandelamido)-3-(2-carboxyethyl-2,3-dihydro-s-triazolo[4,3-b]pyridaain-3-on-6-ylthiomethyl)-3-cephem-4-carboxylic acid, 7-(D-2-nitro-mandelamido)-3-(2-carboxyethyl-2,3-dihydro-s-triazolo[4,3-b]pyridazin-3-on-6-ylthiomethyl)-3-cephem-4-carboxylic acid, 7-(D-3-nitro-mandelamido)-3-(2-carboxyethyl-2,3-dihydro-s-triazolo[4,3-b]pyridazin-3-on-6-ylthiomethyl)-3-cephem-4-carboxylic acid, 7-(D-4-nitro-mandelamido)-3-(2-carboxyethyl-2,3-dihydro-s-triazolo[4,3-b]pyridazin-3-on-6-ylthiomethyl)-3-cephem-4-carboxylic acid, 7-(D-2-hydroxy-mandelamido)-3-(2-carboxyethyl-2,3-dihydro-s-triazolo[4,3-b]pyridazin-3-on-6-ylthiomethyl)-3-cephem-4-carboxylic acid, 7-(D-3-hydroxy-mandelamido)-3-(2-carboxyethyl-2,3-dihydro-s-triazolo[4,3-b]pyridazin-3-on-6-ylthiomethyl)-3-cephem-4-carboxylic acid, 7-(D-4-hydroxy-mandelamido)-3-(2-carboxyethyl-2,3-dihydro-s-triazolo[4,3-b]pyridazin-3-on-6-ylthiomethyl)-3-cephem-4-carboxylic acid, 7-(D-2-methyl-mandelamido)-3-(2-carboxyethyl-2,3-dihydro-s-triazolo[4,3-b]pyridazin-3-on-6-ylthiomethyl)-3-cephem-4-carboxylic acid, 7-(D-3-methyl-mandelamido)-3-(2-carboxyethyl-2,3-dihydro-s-triazolo[4,3-b]pyridazin-3-on-6-ylthiomethyl)-3-cephem-4-carboxylic acid, 7-(D-4-methyl-mandelamido)-3-(2-carboxyethyl-2,3-dihydro-s-triazolo[4,3-b]pyridazin-3-on-6-ylthiomethyl)-3-cephem-4-carboxylic acid, 7-(D-2-methoxy-mandelamido)-3-(2-carboxyethyl-2,3-dihydro-s-triazolo[4,3-b]pyridazin-3-on-6-ylthiomethyl)-3-cephem-4-carboxylic acid, 7-(D-3-methoxy-mandelamido)-3-(2-carboxyethyl-2,3-dihydro-s-triazolo[4,3-b]pyridazin-3-on-6-ylthiomethyl)-3-cephem-4-carboxylic acid, and 7-(D-4-methoxy-mandelamido)-3-(2-carboxyethyl-2,3-dihydro-s-triazolo[4,3-b]pyridazin-3-on-6-ylthiomethyl)-3-cephem-4-carboxylic acid, respectively.

EXAMPLE 12

Substitution for the D-mandelic acid carboxyanhydride in the procedure of Example 10 of an equimolar weight of the carboxyanhydride prepared in similar fashion from D-2-thiopheneglycolic acid and D-3-thiopheneglycolic acid respectively produces 7-(D-α-hydroxy-2-thienylacetamido)-3-(2-carboxyethyl-2,3-dihydro-s-triazolo[4,3-b]pyridazin-3-on-6-ylthiomethyl]-3-cephem-4-carboxylic acid and 7-(D-α-hydroxy-3-thienylacetamido)-3-(2-carboxyethyl-2,3-dihydro-s-triazolo[4,3-b]pyridazin-3-on-6-ylthiomethyl)-3-cephem-4-carboxylic acid, respectively.

There is also provided by the present invention a compound having the formula

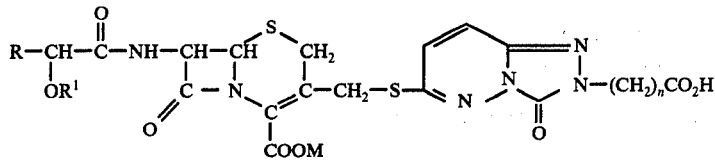

wherein $n$ is one or two, $R^1$ is hydrogen or formyl and R is

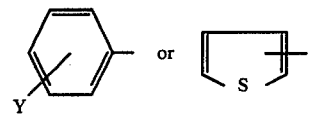

and Y is hydrogen, chlorine, bromine, fluorine, trifluoromethyl, amino, nitro, hydroxy, lower alkyl of 1–4 carbon atoms or lower alkoxy of 1–4 carbon atoms and M is

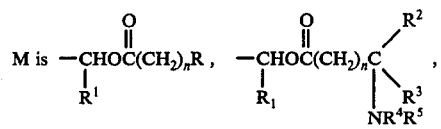

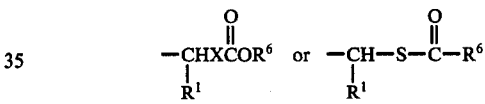

$n$ is 0 to 4; R is hydrogen, alkyl having 1 to 8 carbon atoms, cycloalkyl of 3 to 6 carbon atoms, phenyl, $C_1$–$C_4$ phenalkyl, pyridyl, thienyl, or pyrrolyl; $R^1$ is hydrogen, methyl or ethyl; $R^2$ and $R^3$ are each hydrogen, alkyl having 1 to 6 carbon atoms, phenyl, pyridyl, or thienyl; $R^4$ and $R^5$ are each hydrogen or alkyl of 1 to 4 carbon atoms; $R^6$ is alkyl having 1 to 4 carbon atoms, phenyl, phenalkyl having 1 to 4 carbon atoms, pyridyl, thiadiazolyl, amino or $C_1$–$C_4$ alkylamino; X is NH or oxygen; and each phenyl group is unsubstituted or substituted with one or two substituents selected from the group consisting of alkyl having 1 to 6 carbon atoms, alkoxy having 1 to 4 carbon atoms, hydroxy, amino, $NHR^1$, $N(R^1)_2$, nitro, fluoro, chloro, bromo or carboxy, or a nontoxic, pharmaceutically acceptable salt thereof.

There is also provided by the present invention a compound having the formula

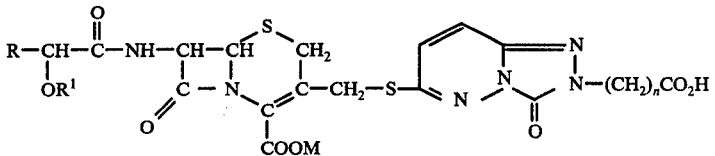

wherein $n$ is one or two, $R^1$ is hydrogen or formyl and R is

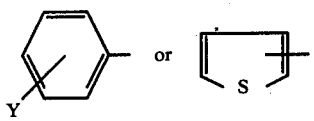

and Y is hydrogen, chlorine, bromine, fluorine, trifluoromethyl, amino, nitro, hydroxy, lower alkyl of 1–4 carbon atoms or lower alkoxy of 1–4 carbon atoms and M is selected from the group consisting of

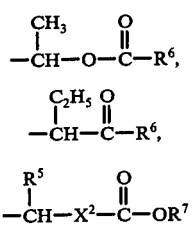

wherein $R^5$ is a hydrogen atom, a methyl or an ethyl group; $X^2$ is —O—, —NH—; $R^6$ is a basic group such as alkyl or aralkyl substituted with substituted or unsubstituted $NH_2$, such as alkyl-$NHCH_3$, aralkyl-$NHCH_3$;

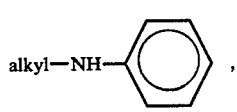

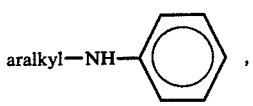

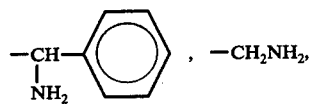

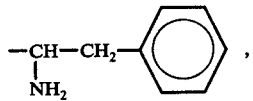

$R^7$ is an alkyl group such as a methyl, ethyl, propyl, isopropyl, butyl, isobutyl, pentyl or 2-ethyl-hexyl group; a cycloalkyl group such as cyclopropyl, cyclobutyl, cyclopentyl, cyclohexyl or cycloheptyl; an aryl group such as phenyl or naphthyl; an aralkyl group such as benzyl or naphthylmethyl; a heterocyclic group and wherein the alkyl, cycloalkyl, aryl, aralkyl and heterocyclic groups may be substituted with one or more groups selected from the class consisting of amino groups, substituted amino groups such as methylamino, diethylamino or acetamido groups, the halogen groups such as fluorine, chlorine or bromine, nitro groups, alkoxy groups such as methoxy, ethoxy, propyloxy, isopropyloxy, butoxy or isobutoxy; or a nontoxic, pharmaceutically acceptable salt thereof.

There is also provided by the present invention a compound having the formula

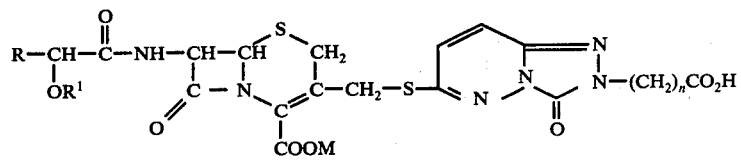

wherein $n$ is one or two, $R^1$ is hydrogen or formyl and R is

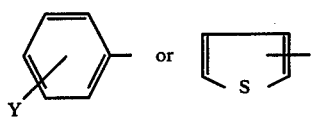

and Y is hydrogen, chlorine, bromine, fluorine, trifluoromethyl, amino, nitro, hydroxy, lower alkyl of 1–4 carbon atoms or lower alkoxy of 1–4 carbon atoms and M is

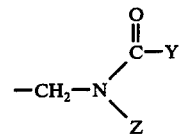

wherein Y is alkyl of one to six carbon atoms, phenyl, benzyl, alkoxy of one to six carbon atoms, or benzyloxy; Z is alkyl of one to six carbon atoms, phenylbenzyl, alkoxy of one to six carbon atoms, cyclopentyl, cyclohexyl and phenyl, or Y+Z taken together are a 3-benzoxazolidine ring; or a nontoxic, pharmaceutically acceptable salt thereof.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterially effective amount of a compound having the formula

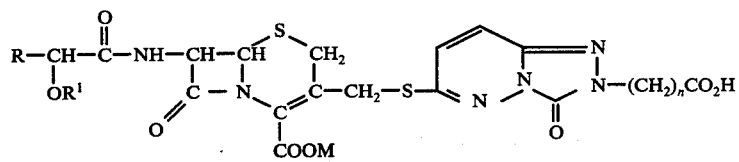

wherein $n$ is one or two, $R^1$ is hydrogen or formyl and R is

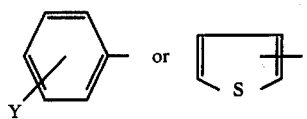

and Y is hydrogen, chlorine, bromine, fluorine, trifluoromethyl, amino, nitro, hydroxy, lower alkyl of 1–4 carbon atoms or lower alkoxy of 1–4 carbon atoms and M is hydrogen, pivaloyloxymethyl, acetoxymethyl, methoxymethyl, acetonyl, phenacyl, p-nitrogenzyl, β,β,β-trichloroethyl, 3-phthalidyl or 5-indanyl and preferably is hydrogen or a nontoxic, pharmaceutically acceptable salt thereof.

There is further provided by the present invention a method of treating bacterial infections comprising administering by injection to an infected warm-blooded animal, including man, an effective but nontoxic dose of 250–1000 mgm. of a compound having the formula

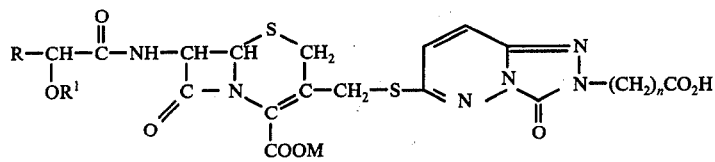

wherein $n$ is one or two, $R^1$ is hydrogen or formyl and R is

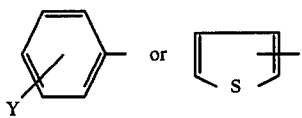

and Y is hydrogen, chlorine, bromine, fluorine, trifluoromethyl, amino, nitro, hydroxy, lower alkyl of 1–4 carbon atoms or lower alkoxy of 1–4 carbon atoms and M is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl or a nontoxic, pharmaceutically acceptable salt thereof.

There is also provided by the present invention a method for combatting Shig. dysenteriae infections which comprises administering to a warm-blooded mammal infected with an Shig. dysenteriae infection an amount effective for treating said Shig. dysenteriae infection of a composition comprising a compound having the formula

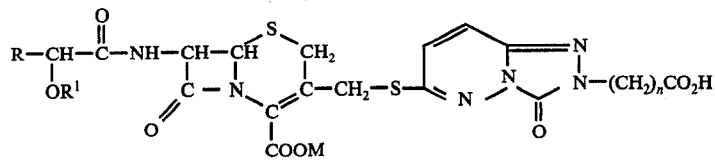

wherein $n$ is one or two, $R^1$ is hydrogen or formyl and R is

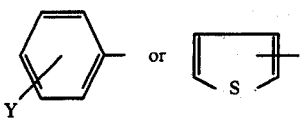

and Y is hydrogen, chlorine, bromine, fluorine, trifluoromethyl, amino, nitro, hydroxy, lower alkyl of 1–4 carbon atoms or lower alkoxy of 1–4 carbon atoms and M is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl and preferably is hydrogen or a nontoxic, pharmaceutically acceptable salt thereof.

There is also provided by the present invention a method for combatting Sal. enteritidis infections which comprises administering to a warm-blooded mammal infected with a Sal. enteritidis infection an amount effective for treating said Sal. enteritidis infection of a composition comprising a compound having the formula

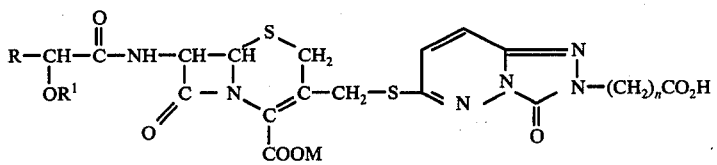

wherein $n$ is one or two, $R^1$ is hydrogen or formyl and R is

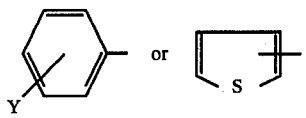

and Y is hydrogen, chlorine, bromine, fluorine, trifluoromethyl, amino, nitro, hydroxy, lower alkyl of 1–4 carbon atoms or lower alkoxy of 1–4 carbon atoms and M is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl and preferably is hydrogen or a nontoxic pharmaceutically acceptable salt thereof.

We claim:

1. An acid having the D configuration in the 7-sidechain and the formula

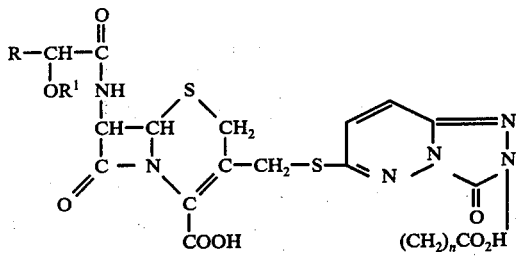

wherein *n* is one or two, R¹ is hydrogen or formyl and R is

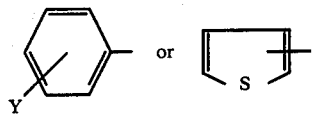

and Y is hydrogen, chlorine, bromine, fluorine, trifluoromethyl, amino, nitro, hydroxy, lower alkyl of 1–4 carbon atoms or lower alkoxy of 1–4 carbon atoms or a nontoxic, pharmaceutically acceptable salt thereof.

2. The sodium salt of an acid of claim 1.

3. The potassium salt of an acid of claim 1.

4. A nontoxic, pharmaceutically acceptable salt of an acid of claim 1.

5. A pivaloyloxymethyl ester of an acid having the D configuration in the 7-sidechain and the formula

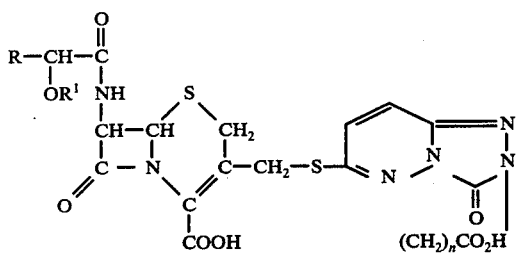

wherein *n* is one or two, R¹ is hydrogen or formyl and R is

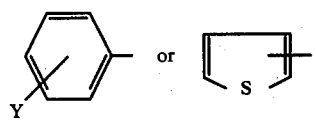

and Y is hydrogen, chlorine, bromine, fluorine, trifluoromethyl, amino, nitro, hydroxy, lower alkyl of 1–4 carbon atoms or lower alkoxy of 1–4 carbon atoms.

6. An acetoxymethyl ester of an acid having the D configuration in the 7-sidechain and the formula

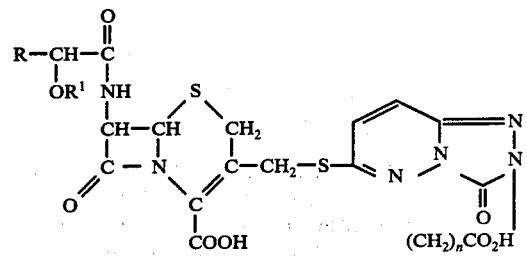

wherein *n* is one or two, R¹ is hydrogen or formyl and R is

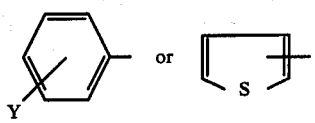

and Y is hydrogen, chlorine, bromine, fluorine, trifluoromethyl, amino, nitro, hydroxy, lower alkyl of 1–4 carbon atoms or lower alkoxy of 1–4 carbon atoms.

7. An acetonyl ester of an acid having the D configuration in the 7-sidechain and the formula

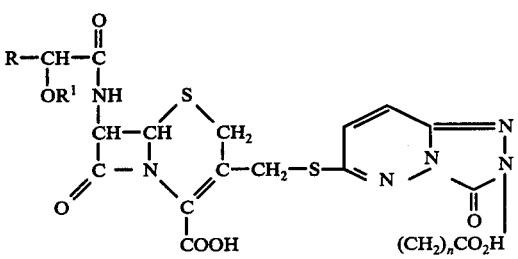

wherein *n* is one or two, R¹ is hydrogen or formyl and R is

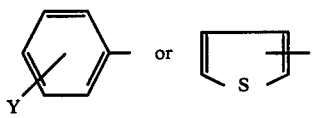

and Y is hydrogen, chlorine, bromine, fluorine, trifluoromethyl, amino, nitro, hydroxy, lower alkyl of 1–4 carbon atoms or lower alkoxy of 1–4 carbon atoms.

8. A phenacyl ester of an acid having the D configuration in the 7-sidechain and the formula

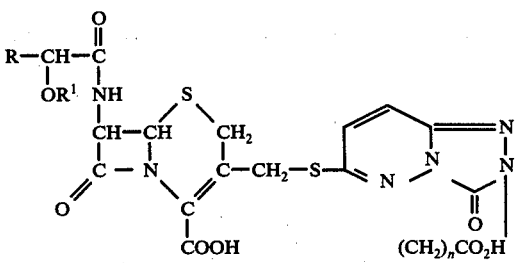

wherein *n* is one or two, R¹ is hydrogen or formyl and R is and Y is hydrogen, chlorine, bromine, fluorine, trifluoromethyl, amino, nitro, hydroxy, lower alkyl of 1–4 carbon atoms or lower alkoxy of 1–4 carbon atoms.

10. An acid having the D configuration in the 7-sidechain and the formula

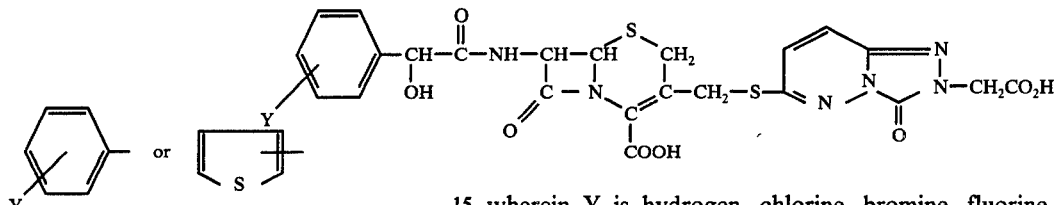

wherein Y is hydrogen, chlorine, bromine, fluorine, trifluoromethyl, amino, nitro, hydroxy, lower alkyl of 1–4 carbon atoms or lower alkoxy of 1–4 carbon atoms or a nontoxic, pharmaceutically acceptable salt thereof.

11. The sodium salt of an acid of claim 10.
12. The potassium salt of an acid of claim 10.
13. The acid of claim 1 having the D configuration in the 7-sidechain and the formula and Y is hydrogen, chlorine, bromine, fluorine, trifluoromethyl, amino, nitro, hydroxy, lower alkyl of 1–4 carbon atoms or lower alkoxy of 1–4 carbon atoms.

9. A methoxymethyl ester of an acid having the D configuration in the 7-sidechain and the formula

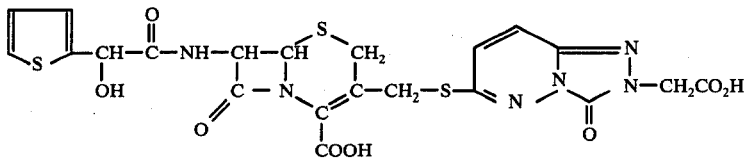

or a nontoxic, pharmaceutically acceptable salt thereof.

14. The sodium salt of the acid of claim 13.
15. The potassium salt of the acid of claim 13.
16. The acid of claim 1 having the D configuration in the 7-sidechain and the formula

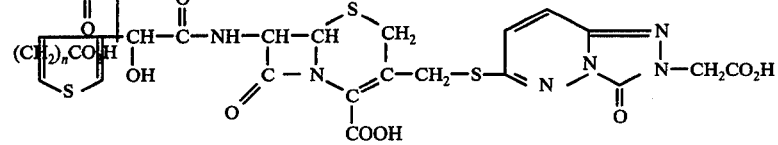

or a nontoxic, pharmaceutically acceptable salt thereof.

17. The sodium salt of the acid of claim 16.
18. The potassium salt of the acid of claim 16.
19. An acid of claim 10 having the D configuration in the 7-sidechain and the formula

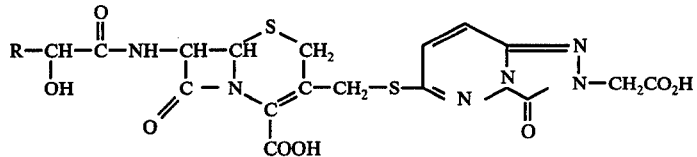

wherein n is one or two, $R^1$ is hydrogen or formyl and R is

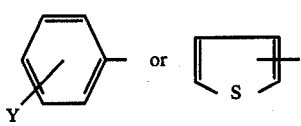

wherein R is chlorophenyl, bromophenyl, trifluoromethylphenyl, tolyl or methoxyphenyl, or a nontoxic, pharmaceutically acceptable salt thereof.

20. The sodium salt of an acid of claim 19.
21. The potassium salt of an acid of claim 19.
22. The acid having the D configuration in the 7-sidechain and the formula

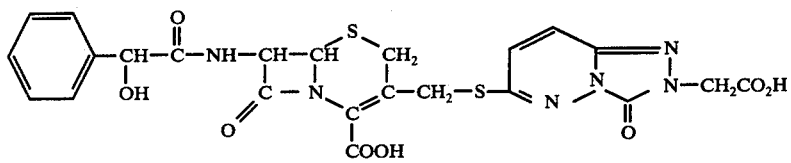

or a nontoxic, pharmaceutically acceptable salt thereof.
23. The sodium salt of the acid of claim 22.
24. The potassium salt of the acid of claim 22.
25. The acid having the D configuration in the 7-sidechain and the formula

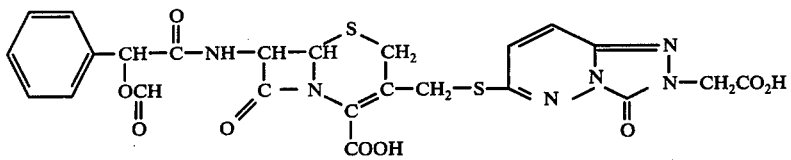

or a nontoxic, pharmaceutically acceptable salt thereof.
26. The sodium salt of the acid of claim 25.
27. The potassium salt of the acid of claim 25.
28. An acid having the D configuration in the 7-sidechain and the formula

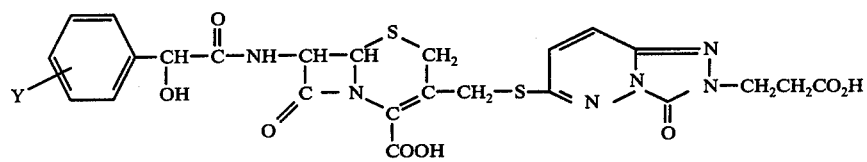

wherein Y is hydrogen, chlorine, bromine, fluorine, trifluoromethyl, amino, nitro, hydroxy, lower alkyl of 1-4 carbon atoms or lower alkoxy of 1-4 carbon atoms or a nontoxic, pharmaceutically acceptable salt thereof.
29. The sodium salt of an acid of claim 28.
30. The potassium salt of an acid of claim 28.

31. The acid of claim 1 having the D configuration in the 7-sidechain and the formula

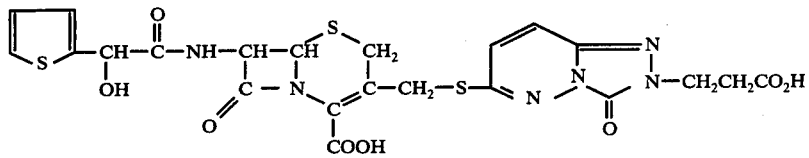

or a nontoxic, pharmaceutically acceptable salt thereof.
32. The sodium salt of the acid of claim 31.
33. The potassium salt of the acid of claim 31.

34. The acid of claim 1 having the D configuration in the 7-sidechain and the formula

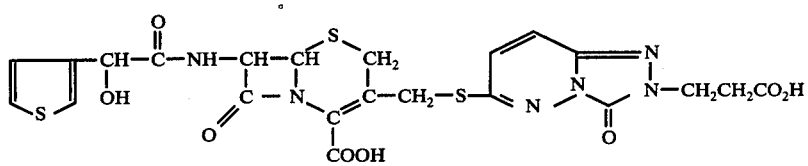

or a nontoxic, pharmaceutically acceptable salt thereof.
35. The sodium salt of the acid of claim 34.
36. The potassium salt of the acid of claim 34.

37. An acid of claim 1 having the D configuration in the 7-sidechain and the formula

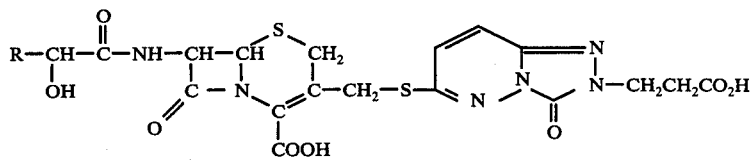

wherein R is chlorophenyl, bromophenyl, trifluoromethylphenyl, tolyl or methoxyphenyl, or a nontoxic, pharmaceutically acceptable salt thereof.
38. The sodium salt of an acid of claim 37.
39. The potassium salt of an acid of claim 37.

40. The acid having the D configuration in the 7-side-chain and the formula

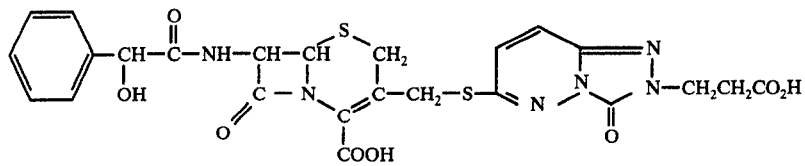

or a nontoxic, pharmaceutically acceptable salt thereof.
41. The sodium salt of the acid of claim 40.
42. The potassium salt of the acid of claim 40.

43. The acid having the D configuration in the 7-side-chain and the formula

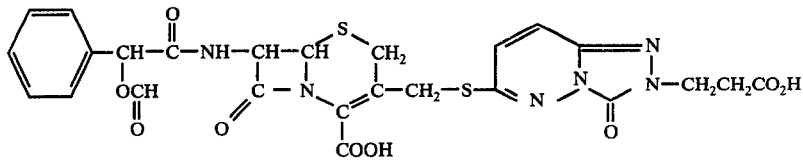

or a nontoxic, pharmaceutically acceptable salt thereof.
44. The sodium salt of the acid of claim 43.
45. The potassium salt of the acid of claim 43.

* * * * *